(12) United States Patent
Jin

(10) Patent No.: US 11,696,931 B2
(45) Date of Patent: *Jul. 11, 2023

(54) BACTERIA FOR TARGETING TUMORS AND TREATING CANCER

(71) Applicant: New Portal Limited, Hong Kong (CN)

(72) Inventor: Ye Jin, Hong Kong (CN)

(73) Assignee: NEW PORTAL LIMITED, Hong Kong (CN)

(*) Notice: Subject to any disclaimer, the term of this patent is extended or adjusted under 35 U.S.C. 154(b) by 640 days.

This patent is subject to a terminal disclaimer.

(21) Appl. No.: 16/644,942

(22) PCT Filed: Aug. 14, 2018

(86) PCT No.: PCT/CN2018/100424
§ 371 (c)(1),
(2) Date: Mar. 5, 2020

(87) PCT Pub. No.: WO2019/047679
PCT Pub. Date: Mar. 14, 2019

(65) Prior Publication Data
US 2020/0323926 A1    Oct. 15, 2020

(30) Foreign Application Priority Data

Sep. 8, 2017 (WO) ................ PCT/CN2017/101069

(51) Int. Cl.
*A61K 35/74*    (2015.01)
*A61P 35/00*    (2006.01)
(Continued)

(52) U.S. Cl.
CPC .............. *A61K 35/74* (2013.01); *A61P 35/00* (2018.01); *C07K 14/245* (2013.01);
(Continued)

(58) Field of Classification Search
CPC .......... A61K 35/74; C12N 15/63; C12N 1/20; C12N 15/635; C12N 15/70; C12N 2810/55; A61P 35/00; C07K 14/245; Y02A 50/30
See application file for complete search history.

(56) References Cited

U.S. PATENT DOCUMENTS

| 5,478,804 A | 12/1995 | Calabresi et al. |
| 6,645,490 B2 | 11/2003 | Yarkoni et al. |

(Continued)

FOREIGN PATENT DOCUMENTS

| CN | 1055879 A | 11/1991 |
| CN | 1420783 A1 | 5/2003 |

(Continued)

OTHER PUBLICATIONS

John F. Toso; et al., Phase I Study of the Intravenous Administration of Attenuated *Salmonella typhimurium* to Patients With Metastatic Melanoma, J Clin Oncol., Jan. 1, 2002, 142-152, 20(1), NIH Public Access.

(Continued)

*Primary Examiner* — Jana A Hines
(74) *Attorney, Agent, or Firm* — Eagle IP Limited

(57) ABSTRACT

Provided is a bacteria for targeting tumors and treating cancer, a drug delivery composition, and methods of using same for treating cancer.

15 Claims, 16 Drawing Sheets

Specification includes a Sequence Listing.

(51) Int. Cl.
 C07K 14/245 (2006.01)
 C12N 15/63 (2006.01)
 C12N 15/70 (2006.01)
(52) U.S. Cl.
 CPC ........... *C12N 15/635* (2013.01); *C12N 15/70* (2013.01); *C12N 2810/55* (2013.01)

(56) References Cited

U.S. PATENT DOCUMENTS

| | | |
|---|---|---|
| 9,198,950 B2 | 12/2015 | Mellata |
| 9,555,127 B2 | 1/2017 | Cueva-Mendez |
| 9,889,164 B2 | 2/2018 | Falb et al. |
| 2018/0325963 A1 | 11/2018 | Isabella et al. |
| 2020/0323926 A1 | 10/2020 | Jin |

FOREIGN PATENT DOCUMENTS

| | | | |
|---|---|---|---|
| CN | 1688699 A | 10/2005 | |
| CN | 101010002 A1 | 8/2007 | |
| CN | 104498418 A | 4/2015 | |
| CN | 105483067 A | 4/2016 | |
| CN | 106676119 A | 5/2017 | |
| CN | 107636146 A | 1/2018 | |
| CN | 110527655 A | 12/2019 | |
| CN | 111246865 A1 | 6/2020 | |
| CN | 111315868 A | 6/2020 | |
| EP | 2543720 A1 | 1/2013 | |
| EP | 2543720 A1 * | 1/2013 | ............. C12N 15/70 |
| IN | 201403506 I3 | 7/2016 | |
| TW | 201206472 A | 2/2012 | |
| WO | 9958652 A2 | 11/1999 | |
| WO | 9958652 A3 | 1/2000 | |
| WO | 2001005421 A1 | 1/2001 | |
| WO | 2009098246 A1 | 8/2009 | |
| WO | 2012087483 A1 | 6/2012 | |
| WO | WO-2012087483 A1 * | 6/2012 | ........... A61K 38/164 |
| WO | 2016106343 A1 | 6/2016 | |
| WO | 2016141108 A1 | 9/2016 | |
| WO | 2016183531 A1 | 11/2016 | |
| WO | 2016185471 A1 | 11/2016 | |
| WO | 2016210373 A2 | 12/2016 | |
| WO | 2015118541 A1 | 7/2020 | |
| WO | 2020151185 A1 | 7/2020 | |

OTHER PUBLICATIONS

Christopher Groth; et al., Immunosuppression mediated by myeloid-derived suppressor cells (MDSCs) during tumour progression, British Journal of Cancer, 2019, 16-25; 120, Cancer Research UK.
Dmitry I. Gabrilovich; et al., Coordinated regulation of myeloid cells by tumours, Nat Rev Immunol. Apr. 1, 2013, 253-268, 12(4), NIH Public Access.
J. Martin Brown, Tumor Microenvironment and the Response to Anticancer Therapy, Cancer Biology & Therapy, Aug. 13, 2002, 453-458, 1:5, Landes Bioscience.
Hyun Min Jeon; et al., Early growth response 1 regulates glucose deprivation-induced necrosis, Oncology Reports, 2013, 669-675, 29.
Whisstock J; et al., Prediction of protein function from protein sequence and structure. Quarterly Reviews of Biophysics, Aug. 2003, 307-340, 36(3), Cambridge University Press London.
Andrzej Witkowski; et al., Conversion of a β-Ketoacyl Synthase to a Malonyl Decarboxylase by Replacement of the Active-Site Cysteine with Glutamine, Biochemistry, Aug. 18, 1999, 11643-11650, 38, American Chemical Society.
Lev Kisselev, Polypeptide Release Factors in Prokaryotes and Eukaryotes: Same Function, Different Structure, Structure, Jan. 8-9, 2002, 10, Elsevier Science Ltd.
Adam T St Jean; et al., Bacterial delivery of *Staphylococcus aureus* α-hemolysin causes regression and necrosis in murine tumors, Molecular Therapy, 2014, 1266-1274, vol. 22, No. 7.

RM Ryan; et al.; Bacterial delivery of a novel cytolysin to hypoxic areas of solid tumors, Gene Therapy, 2009, 329-339, vol. 16, Macmillan Publishers Ltd.
Engelbart, K. & Gericke, D. (1964). Oncolysis by Clostridia. V. Transplanted Tumors of the Hamster. Cancer Res 24, 239-242.
Thiele, E. H., Arison, R. N. & Boxer, G. E. (1964). Oncolysis by Clostridia. Iv. Effect of Nonpathogenic Clostridial Spores in Normal and Pathological Tissues. Cancer Res 24, 234-238.
Sasaki, T. et al. (2006). Genetically engineered Bifidobacterium longum for tumor-targeting enzyme-prodrug therapy of autochthonous mammary tumors in rats. Cancer science 97, 649-657.
Yazawa, K. et al. (2001). Bifidobacterium longum as a delivery system for gene therapy of chemically induced rat mammary tumors. Breast Cancer Res Treat 66, 165-170.
Lee, C. H., Wu, C. L. & Shiau, A. L. (2008). *Salmonella choleraesuis* as an anticancer agent in a syngeneic model of orthotopic hepatocellular carcinoma. Int J Cancer 122, 930-935.
Pawelek, J. M., Low, K. B. & Bermudes, D. (1997). Tumor-targeted *Salmonella* as a novel anticancer vector. Cancer Res 57, 4537-4544.
Sznol, M., Lin, S. L., Bermudes, D., Zheng, L. M. & King, I. (2000). Use of preferentially replicating bacteria for the treatment of cancer. J Clin Invest 105, 1027-1030.
Cronin, M. et al. (2012). High resolution in vivo bioluminescent imaging for the study of bacterial tumour targeting. PLoS One 7, e30940.
Stritzker, J. et al. (2007). Tumor-specific colonization, tissue distribution, and gene induction by probiotic *Escherichia coli* Nissle 1917 in live mice. International journal of medical microbiology : IJMM 297, 151-162.
Krick, E. L. et al. (2012). Evaluation of Clostridium novyi-NT spores in dogs with naturally occurring tumors. American journal of veterinary research 73, 112-118.
Roberts, N. J. et al. (2014). Intratumoral injection of Clostridium novyi-NT spores induces antitumor responses. Science translational medicine 6, 249ra111.
Min, J. J. et al. (2008). Noninvasive real-time imaging of tumors and metastases using tumor-targeting light-emitting *Escherichia coli*. Molecular imaging and biology : MIB : the official publication of the Academy of Molecular Imaging 10, 54-61.
Yu, B. et al. (2012). Explicit hypoxia targeting with tumor suppression by creating an "obligate" anaerobic *Salmonella typhimurium* strain. Sci Rep 2, 436.
Frahm, M. et al. (2015). Efficiency of conditionally attenuated *Salmonella enterica* serovar Typhimurium in bacterium-mediated tumor therapy. mBio 6(2):e00254-15.
Stern, C. et al. (2015). Induction of CD4(+) and CD8(+) anti-tumor effector T cell responses by bacteria mediated tumor therapy. Int J Cancer 137, 2019-2028.
Hirayama, A. et al. (2009). Quantitative metabolome profiling of colon and stomach cancer microenvironment by capillary electrophoresis time-of-flight mass spectrometry. Cancer Res 69, 4918-4925.
Urasaki, Y., Heath, L. & Xu, C. W. (2012). Coupling of glucose deprivation with impaired histone H2B monoubiquitination in tumors. PLoS One 7, e36775.
Jacob, F. & Monod, J. (1961). Genetic regulatory mechanisms in the synthesis of proteins. J Mol Biol 3, 318-356.
Afif, H., Allali, N., Couturier, M. & Van Melderen, L. (2001). The ratio between CcdA and CcdB modulates the transcriptional repression of the ccd poison-antidote system. Mol Microbiol 41, 73-82.
Zhao, M. et al. (2005). Tumor-targeting bacterial therapy with amino acid auxotrophs of GFP-expressing *Salmonella typhimurium*. Proc Natl Acad Sci U S A 102, 755-760.
Diaz, L. A., Jr. et al. (2005). Pharmacologic and toxicologic evaluation of C. novyi-NT spores. Toxicological sciences : an official journal of the Society of Toxicology 88, 562-575.
Z. Douvlis. (1999) Interference of amino acid patterns and tissue-specific amino acids absorption dominance under the influence of tumor cell protein degradation toxins Medical Hypotheses No. 53 (5), 450-457.
Guillermo De La Cueva-Mendez et al. (2003) Regulatable killing of eukaryotic cells by the prokaryotic proteins Kid and Kis The EMBO Journal No. 22 (2), 246-251.

(56) References Cited

OTHER PUBLICATIONS

Lukasz Wieteska et al. (2014)Toxins VapC and PasB from prokaryotic TA modules remain active in mammalian cancer cells Toxins No. 6, 2948-2931.

Yeo, Chewchieng et al.(2016) Heterologous expression of toxins from bacterial Toxin-Antitoxin Systems in eukaryotic cells: stralegies and applications Toxins No. 49 (8), 1-16.

Smith, M.A., et al. (2015). Antibodies against hemolysin and cytotoxic necrotizing factor type 1 (CNF1) reduce bladder inflammation in a mouse model of urinary tract infection with toxigenic uropathogenic *Escherichia coli*. Infect Immun 83, 1661-1673.

Zhao, M., et al. (2006). Targeted therapy with a *Salmonella typhimurium* leucine-arginine auxotroph cures orthotopic human breast tumors in nude mice. Cancer Res 66, 7647-7652.

Fensterle J et al. (2008) Cancer immunotherapy based on recombinant *Salmonella enterica* serovar Typhimurium aroA strains secreting prostate-specific antigen and cholera toxin subunit B. Cancer Gene Ther. Feb;15(2):85-93.

Shimazu T, et al. (2014) Regression of solid tumors by induction of MazF, a bacterial mRNA endoribonuclease. J Mol Microbiol Biotechnol. 24(4):228-33.

Bakhtiari R, et al. (2016) Rising Cellular Immune Response after Injection of pVax/iutA: A Genetic DNA Cassette as Candidate Vaccine against Urinary Tract Infection. Iran J Public Health. 45(7):890-6.

Goodall ECA, et al. (2018) The Essential Genome of *Escherichia coli* K-12. mBio. Feb. 20, 2018;9(1):e02096-17.

Habibi M, et al. (2017) Evaluation of prevalence, immunogenicity and efficacy of FyuA iron receptor in uropathogenic *Escherichia coli* isolates as a vaccine target against urinary tract infection. Microb Pathog. Sep;110:477-483.

Hur J, et al. (2017) Ontology-based literature mining of *E. coli* vaccine-associated gene interaction networks. J Biomed Semantics. Mar. 14;8(1):12.

Jiang, S.N., et al. (2010). Inhibition of tumor growth and metastasis by a combination of *Escherichia coli*-mediated cytolytic therapy and radiotherapy. Molecular therapy : the journal of the American Society of Gene Therapy 18, 635-642.

Leventhal, D.S, et al. (2020). Immunotherapy with engineered bacteria by targeting the STING pathway for anti-tumor immunity. Nature communications 11, 2739.

Nichols, K.B., et al. (2016). Molecular Characterization of the Vacuolating Autotransporter Toxin in Uropathogenic *Escherichia coli*. J Bacteriol 198, 1487-1498.

Quispe-Tintaya, W., et al.(2013). Nontoxic radioactive Listeria(at) is a highly effective therapy against metastatic pancreatic cancer. Proc Natl Acad Sci U S A 110, 8668-8673.

The Present Study Situation on the Application of Staphylococcal Enterotoxin B (SEB)in Tumor Therapy, (2002) Journal of Microbiology July vol. 22 No. 4.

Jin M., (2000) "Tumor-targeted bacterial as a novelanti-cancer vector" China Biotechnology 20.2 : 49-51.

Olivier Epaulard, et al. (2008) Optimization of a type III secretion system-based Pseudomonas aeruginosa live vector for antigen delivery. Clinical and Vaccine Immunology, American Society for Microbiology, 5 (2), pp. 308-313.

Forbes N. S. (2010). Engineering the perfect (bacterial) cancer therapy. Nature reviews. Cancer, 10(11), 785-794.

Gazit, G., Hung, G., Chen, X., Anderson, W. F., & Lee, A. S. (1999). Use of the glucose starvation-inducible glucose-regulated protein 78 promoter in suicide gene therapy of murine fibrosarcoma. Cancer research, 59(13), 3100-3106.

Jean, A. T. S., Swofford, C. A., Panteli, J. T., Brentzel, Z. J., & Forbes, N. S. (2014). Bacterial delivery of *Staphylococcus aureus* α-hemolysin causes regression and necrosis in murine tumors. Molecular Therapy, 22(7), 1266-1274.

Dhakal, B.K., and Mulvey, M.A. (2012). The UPEC pore-forming toxin alpha-hemolysin triggers proteolysis of host proteins to disrupt cell adhesion, inflammatory, and survival pathways. Cell host & microbe 11, 58-69.

Elsen, S., Huber, P., Bouillot, S., et al. (2014). A type III secretion negative clinical strain of Pseudomonas aeruginosa employs a two-partner secreted exolysin to induce hemorrhagic pneumonia. Cell host & microbe 15, 164-176.

Gur, C., Coppenhagen-Glazer, et al. (2013). Natural killer cell-mediated host defense against uropathogenic *E. coli* is counteracted by bacterial hemolysinA-dependent killing of NK cells. Cell host & microbe 14, 664-674.

Huntley, J.S., Sathyamoorthy, V., et al. (1997). Membrane attack induced by HlyA, a pore-forming toxin of Vibrio cholerae. Human & experimental toxicology 16, 101-105.

Li, M., Zhang, Y., Liu, Z., et al. (2007). Aberrant expression of zinc transporter ZIP4 (SLC39A4) significantly contributes to human pancreatic cancer pathogenesis and progression. Proc Natl Acad Sci U S A 104, 18636-18641.

Liu, X., Ding, S., Shi, P., et al. (2017). Non-hemolytic enterotoxin of Bacillus cereus induces apoptosis in Vero cells. Cellular microbiology 19.

Reboud, E., Elsen, S., et al. (2016). Phenotype and toxicity of the recently discovered exlA-positive Pseudomonas aeruginosa strains collected worldwide. Environmental microbiology 18, 3425-3439.

Sastalla, I., Fattah, R., et al. (2013). The Bacillus cereus Hbl and Nhe tripartite enterotoxin components assemble sequentially on the surface of target cells and are not interchangeable. PLoS One 8, e76955.

Sathyamoorthy, V., et al. (1997). Biochemical and physiological characteristics of HlyA, a pore-forming cytolysin of Vibrio cholerae serogroup O1. Toxicon 35, 515-527.

Sebastian Felgner, et al. (Aug. 3, 2017) Tumour-targeting bacteria-based cancer therapies for increased specificity and improved outcome Microb Biotechnol. No. 5 vol. 10 ISSN: 1751-7915.

\* cited by examiner liver abscess, SH1hly group

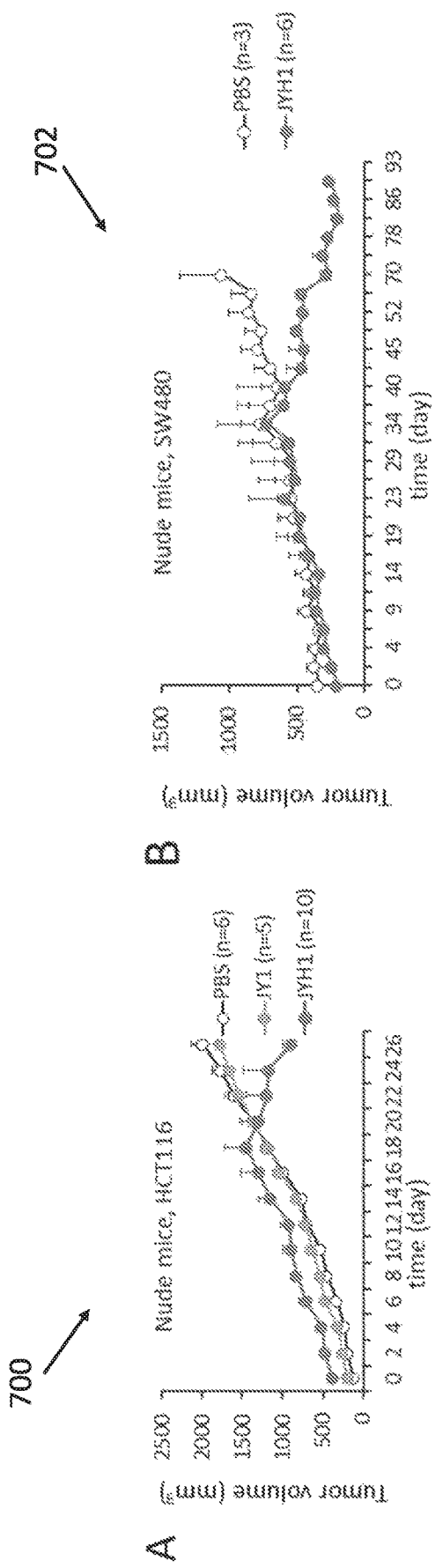

SEQUENCE LISTING

<160> NUMBER OF SEQ ID NOS: 13

<210> SEQ ID NO 1
<211> LENGTH: 306
<212> TYPE: DNA
<213> ORGANISM: Escherichia coli

<400> SEQUENCE: 1
atgcagttta aggtttacac ctataaaaga gagagccgtt atcgtctgtt tgtggatgta 60
cagagtgata ttattgacac gcccgggcga cggatggtga tccccctggc cagtgcacgt 120
ctgctgtcag ataaagtctc ccgtgaactt tacccggtgg tgcatatcgg ggatgaaagc 180
tggcgcatga tgaccaccga tatggccagt gtgccggtct ccgttatcgg ggaagaagtg 240
gctgatctca gccaccgcga aaatgacatc aaaaacgcca ttaacctgat gttctgggga 300
atataa 306

<210> SEQ ID NO 2
<211> LENGTH: 219
<212> TYPE: DNA
<213> ORGANISM: Escherichia coli

<400> SEQUENCE: 2
atgaagcagc gtattacagt gacagttgac agcgacagct atcagttgct caaggcatat 60
gatgtcaata tctccggtct ggtaagcaca accatgcaga atgaagcccg tcgtctgcgt 120
gccgaacgct ggaaagcgga aaatcaggag gggatggctg aggtcgcccg gtttattgaa 180
atgaacggct cttttgctga tgagaacagg gactggtga 219

<210> SEQ ID NO 3
<211> LENGTH: 164
<212> TYPE: DNA
<213> ORGANISM: Escherichia coli

<400> SEQUENCE: 3
taatgcagct ggcacgacag gtttcccgac tggaaagcgg gcagtgagcg caacgcaatt 60
aatgtgagtt agctcactca ttaggcaccc caggctttac actttatgct tccggctcgt 120
atgttgtgtg gaattgtgag cggataacaa tttcacacag gaaa 164

<210> SEQ ID NO 4
<211> LENGTH: 1101
<212> TYPE: DNA
<213> ORGANISM: Escherichia coli

<400> SEQUENCE: 4

| | | | | | |
|---|---|---|---|---|---|
| ataacttcgt | ataatgtatg | ctatacgaag | ttattaggtc | tgaagaggag | tttacgtcca | 60 |
| gccaagctta | ggatcccggg | taccgatatc | ggcagcatca | cccgacggac | tttgcgccga | 120 |
| ataaatacct | gtgacggaag | atcacttcgc | agaataaata | aatcctggtg | tccctgttga | 180 |
| taccgggaag | ccctgggcca | acttttggcg | aaaatgagac | gttgatcggc | acgtaagagg | 240 |
| ttccaacttt | caccataatg | aagtaagatc | actaccgggc | gtattttttg | agttatcgag | 300 |
| attttcagga | gctaaggaag | ctaaaatgga | gaaaaaatc | actggatata | ccaccgttga | 360 |
| tatatcccaa | tggcatcgta | aagaacattt | tgaggcattt | cagtcagttg | ctcaatgtac | 420 |
| ctataaccag | accgttcagc | tggatattac | ggcctttta | aagaccgtaa | agaaaaataa | 480 |
| gcacaagttt | tatccggcct | ttattcacat | tcttgcccgc | cagatgaatg | ctcatccgga | 540 |
| attccgtatg | gcaatgaaag | acggtgagct | ggtgatatgg | gatagtgttc | acccttgtta | 600 |
| caccgttttc | catgagcaaa | ctgaaacgtt | ttcatcgctc | tggagtgaat | accacgacga | 660 |
| tttccggcag | tttctacaca | tatattcgca | agatgtggcg | tgttacggtg | aaaacctggc | 720 |
| ctatttccct | aaagggttta | ttgagaatat | gttttcgtc | tcagccaatc | cctgggtgag | 780 |
| tttcaccagt | tttgatttaa | acgtggccaa | tatggacaac | ttcttcgccc | cgttttcac | 840 |
| catgggcaaa | tattatacgc | aaggcgacaa | ggtgctgatg | ccgctgacga | ttcaggttca | 900 |
| tcatgccgtt | tgtgatggct | tccatgtcgg | cagaatgctt | aatgaattac | aacagtactg | 960 |
| cgatgagtgg | cagggcgggg | cgtaattttt | ttaaggcagt | tattggtgcc | cttagatatc | 1020 |
| aagcttagga | tccggaaccc | ttaatataac | ttcgtataat | gtatgctata | cgaagttatt | 1080 |
| aggtccctcg | aagaggttca | c | | | | 1101 |

<210> SEQ ID NO 5
<211> LENGTH: 342
<212> TYPE: DNA
<213> ORGANISM: Escherichia coli

<400> SEQUENCE: 5

| | | | | | |
|---|---|---|---|---|---|
| aacgcgtgga | tccggcttac | taaaagccag | ataacagtat | gcgtatttgc | gcgctgattt | 60 |
| ttgcggtata | agaatatata | ctgatatgta | tacccgaagt | atgtcaaaaa | gaggtgtgct | 120 |
| atgaagcagc | gtattacagt | gacagttgac | agcgacagct | atcagttgct | caaggcatat | 180 |
| atgatgtcaa | tatctccggt | ctggtaagca | caaccatgca | gaatgaagcc | gtcgtctgc | 240 |
| gtgccgaacg | ctggaaagcg | gaaaatcagg | aagggatggc | tgaggtcgcc | cggtttattg | 300 |
| aaatgaacgg | ctcttttgct | gacgagaaca | gggactggtg | aa | | 342 |

<210> SEQ ID NO 6
<211> LENGTH: 158
<212> TYPE: DNA
<213> ORGANISM: Escherichia coli

<400> SEQUENCE: 6

| | | | | | |
|---|---|---|---|---|---|
| tgcctggcgg | cagtagcgcg | gtggtccac | ctgaccccat | gccgaactca | gaagtgaaac | 60 |
| gccgtagcgc | cgatggtagt | gtggggtctc | cccatgcgag | agtagggaac | tgccaggcat | 120 |
| caaataaaac | gaaaggctca | gtcgaaagac | tgggcctt | | | 158 |

<210> SEQ ID NO 7
<211> LENGTH: 2710
<212> TYPE: DNA
<213> ORGANISM: Artificial Sequence
<220> FEATURE:
<223> OTHER INFORMATION: nucleic acid system of one example embodiment

<400> SEQUENCE: 7

```
aacgcgtgga tccggcttac taaaagccag ataacagtat gcgtatttgc gcgctgattt      60
ttgcggtata agaatatata ctgatatgta tacccgaagt atgtcaaaaa gaggtgtgct     120
atgaagcagc gtattacagt gacagttgac agcgacagct atcagttgct caaggcatat     180
atgatgtcaa tatctccggt ctggtaagca caaccatgca gaatgaagcc gtcgtctgc      240
gtgccgaacg ctggaaagcg gaaaatcagg aagggatggc tgaggtcgcc cggtttattg     300
aaatgaacgg ctcttttgct gacgagaaca gggactggtg aaatgcagtt aaggtttac      360
acctataaaa gagagagccg ttatcgtctg tttgtggatg tacagagtga tattattgac     420
acgcccgggc gacggatggt gatccccctg ccagtgcac gtctgctgtc agataaagtc      480
tcccgtgaac tttacccggt ggtgcatatc ggggatgaaa gctggcgcat gatgaccacc     540
gatatggcca gtgtgccggt ctccgttatc ggggaagaag tggctgatct cagccaccgc     600
gaaaatgaca tcaaaaacgc cattaacctg atgttctggg aatataaat gtcaggctcc      660
gttatacaca gccagtctgc aggtcgacca tagtgactgg atatgttgtg ttttacagta     720
ttatgtagtc tgttttttat gcaaaatcta atttaatata ttgatattta tatcatttta    780
cgtttctcgt tcagctttct tgtacaaagt ggtgatcaag cttgaaggta agcctatccc     840
taaccctctc ctcggtctcg attctacgcg taccggtcat catcaccatc accattgagt     900
ttaaacggtc tccagcttgg ctgttttggc ggatgagaga agattttcag cctgatacag     960
attaaatcag aacgcagaag cggtctgata aaacagaatt tgcctggcgg cagtagcgcg    1020
gtggtcccac ctgaccccat gccgaactca gaagtgaaac gccgtagcgc cgatggtagt    1080
gtggggtctc cccatgcgag agtagggaac tgccaggcat caaataaaac gaaaggctca    1140
gtcgaaagac tgggccttaa taggcgtatc acgaggccct ttcgtcttca agaattccga    1200
tcatattcaa taaccccttaa tataacttcg tataatgtat gctatacgaa gttattaggt    1260
ctgaagagga gtttacgtcc agccaagctt aggatcccgg gtaccgatat cggcagcatc    1320
acccgacgga ctttgcgccg aataaatacc tgtgacggaa gatcacttcg cagaataaat    1380
aaatcctggt gtcccgtttg ataccgggaa gccctgggcc aacttttggc gaaaatgaga    1440
cgttgatcgg cacgtaagag gttccaactt tcaccataat gaagtaagat cactaccggg    1500
cgtattttt gagttatcga gattttcagg agctaaggaa gctaaaatgg agaaaaaat     1560
cactggatat accaccgttg atatatccca atggcatcgt aaagaacatt ttgaggcatt    1620
tcagtcagtt gctcaatgta cctataacca gaccgttcag ctggatatta cggcctttt     1680
aaagaccgta agaaaaaata agcacaagtt ttatccggcc tttattcaca ttcttgcccg    1740
ccagatgaat gctcatccgg aattccgtat ggcaatgaaa gacggtgagc tggtgatatg    1800
ggatagtgtt cacccttgtt acaccgtttt ccatgagcaa actgaaacgt ttcatcgct     1860
ctggagtgaa taccacgacg atttccggca gtttctacac atatattcgc aagatgtggc    1920
gtgttacggt gaaaacctgg cctatttccc taaagggttt attgagaata tgttttttcgt    1980
ctcagccaat ccctgggtga gtttcaccag ttttgattta aacgtggcca atatggacaa    2040
```

```
cttcttcgcc cccgttttca ccatgggcaa atattatacg caaggcgaca aggtgctgat    2100
gccgctgacg attcaggttc atcatgccgt ttgtgatggc ttccatgtcg cagaatgct    2160 taatgaatta caacagtact gcgatgagtg gcagggcggg gcgtaatttt tttaaggcag    2220
ttattggtgc ccttagatat caagcttagg atccggaacc cttaatataa cttcgtataa    2280
tgtatgctat acgaagttat taggtccctc gaagaggttc actaatgcag ctggcacgac    2340
aggtttcccg actggaaagc gggcagtgag cgcaacgcaa ttaatgtgag ttagctcact    2400
cattaggcac cccaggcttt acactttatg cttccggctc gtatgttgtg tggaattgtg    2460
agcggataac aatttcacac aggaaatgtc tatgaagcag cgtattacag tgacagttga    2520
cagcgacagc tatcagttgc tcaaggcata tgatgtcaat atctccggtc tggtaagcac    2580
aaccatgcag aatgaagccc gtcgtctgcg tgccgaacgc tggaaagcgg aaaatcagga    2640
ggggatggct gaggtcgccc ggtttattga aatgaacggc tcttttgctg atgagaacag    2700
ggactggtga                                                           2710

<210> SEQ ID NO 8
<211> LENGTH: 2710
<212> TYPE: DNA
<213> ORGANISM: Artificial Sequence
<220> FEATURE:
<223> OTHER INFORMATION: Nucleic acid system of another example
      embodiment

<400> SEQUENCE: 8
aacgcgtgga tccggcttac taaaagccag ataacagtat gcgtatttgc gcgctgattt      60
ttgcggtata agaatatata ctgatatgta tacccgaagt atgtcaaaaa gaggtgtgct     120
atgaagcagc gtattacagt gacagttgac agcgacagct atcagttgct caaggcatat     180
atgatgtcaa tatctccggt ctggtaagca caaccatgca gaatgaagcc cgtcgtctgc     240
gtgccgaacg ctggaaagcg gaaaatcagg aagggatggc tgaggtcgcc cggtttattg     300
aaatgaacgg ctcttttgct gacgagaaca gggactggtg aaatgcagtt taaggtttac     360
acctataaaa gagagagccg ttatcgtctg tttgtggatg tacagagtga atattattgac    420 acgcccggc gacggatggt gatccccctg ccagtgcac gtctgctgtc agataaagtc      480
tcccgtgaac tttacccggt ggtgcatatc ggggatgaaa gctggcgcat gatgaccacc     540
gatatggcca gtgtgccggt ctccgttatc ggggaagaag tggctgatct cagccaccgc    600
gaaaatgaca tcaaaaacgc cattaacctg atgttctggg aatataaat gtcaggctcc    660 gttatacaca gccagtctgc aggtcgacca tagtgactgg atatgttgtg ttttacagta    720
ttatgtagtc tgttttttat gcaaaatcta atttaatata ttgatattta tatcatttta    780
cgtttctcgt tcagctttct tgtacaaagt ggtgatcaag cttgaaggta agcctatccc    840
taaccctctc ctcggtctcg attctacgcg taccggtcat catcaccatc accattgagt    900
ttaaacggtc tccagcttgg ctgttttggc ggatgagaga agattttcag cctgatacag    960
attaaatcag aacgcagaag cggtctgata aaacagaatt tgcctggcgg cagtagcgcg    1020
gtggtcccac ctgaccccat gccgaactca gaagtgaaac gccgtagcgc cgatggtagt    1080
gtggggtctc cccatgcgag agtagggaac tgccaggcat caaataaaac gaaaggctca    1140
gtcgaaagac tgggccttaa taggcgtatc acgaggccct tcgtcttca agaattccga    1200 tcatattcaa taacccttaa tataacttcg tataatgtat gctatacgaa gttattaggt    1260
ctgaagagga gtttacgtcc agccaagctt aggatcccgg gtaccgatat cggcagcatc    1320
```

```
acccgacgga ctttgcgccg aataaatacc tgtgacggaa gatcacttcg cagaataaat    1380
aaatcctggt gtccctgttg ataccgggaa gccctgggcc aacttttggc gaaaatgaga    1440
cgttgatcgg cacgtaagag gttccaactt tcaccataat gaagtaagat cactaccggg    1500 cgtattttt gagttatcga gattttcagg agctaaggaa gctaaaatgg agaaaaaat     1560 cactggatat accaccgttg atatatccca atggcatcgt aaagaacatt ttgaggcatt    1620
tcagtcagtt gctcaatgta cctataacca gaccgttcag ctggatatta cggccttttt    1680
aaagaccgta agaaaaata agcacaagtt ttatccggcc tttattcaca ttcttgcccg    1740
ccagatgaat gctcatccgg aattccgtat ggcaatgaaa gacggtgagc tggtgatatg    1800
ggatagtgtt caccccttgtt acaccgtttt ccatgagcaa actgaaacgt tttcatcgct    1860
ctggagtgaa taccacgacg atttccggca gtttctacac atatattcgc aagatgtggc    1920
gtgttacggt gaaaacctgg cctatttccc taaagggttt attgagaata tgttttttcgt    1980 ctcagccaat ccctgggtga gtttcaccag ttttgattta aacgtggcca atatggacaa    2040
cttcttcgcc cccgttttca ccatgggcaa atattatacg caaggcgaca aggtgctgat    2100
gccgctgacg attcaggttc atcatgccgt ttgtgatggc ttccatgtcg gcagaatgct    2160
taatgaatta aacagtact gcgatgagtg gcagggcggg gcgtaatttt tttaaggcag    2220
ttattggtgc ccttagatat caagcttagg atccggaacc cttaatataa cttcgtataa    2280
tgtatgctat acgaagttat taggtccctc gaagaggttc actaatgcag ctggcacgac    2340
aggtttcccg actggaaagc gggcagtgag cgcaacgcaa ttaatgtgag ttagctcact    2400
cattaggcac cccaggcttt acactttatg cttccggctc gtatgttgtg tggaattgtg    2460
agcggataac aatttcacac aggaaagcct tatgaagcag cgtattacag tgacagttga    2520
cagcgacagc tatcagttgc tcaaggcata tgatgtcaat atctccggtc tggtaagcac    2580
aaccatgcag aatgaagccc gtcgtctgcg tgccgaacgc tggaaagcgg aaaatcagga    2640
ggggatggct gaggtcgccc ggtttattga aatgaacggc tcttttgctg atgagaacag    2700
ggactggtga                                                           2710
```

<210> SEQ ID NO 9
<211> LENGTH: 66
<212> TYPE: DNA
<213> ORGANISM: Artificial Sequence
<220> FEATURE:
<223> OTHER INFORMATION: pelB leader sequence

<400> SEQUENCE: 9

```
atgaaatacc tgctgccgac cgctgctgct ggtctgctgc tcctcgctgc ccagccggcg    60
atggcc                                                               66
```

<210> SEQ ID NO 10
<211> LENGTH: 5019
<212> TYPE: DNA
<213> ORGANISM: Artificial Sequence
<220> FEATURE:
<223> OTHER INFORMATION: exlA with pelB leader sequence

<400> SEQUENCE: 10

```
atgaaatacc tgctgccgac cgctgctgct ggtctgctgc tcctcgctgc ccagccggcg    60
atggcccata gagacaatcc tgtcttccac ctctccccc ggggaaaact ccgttgcctg    120
atcgccggcc tgctgctggc gccccacctg ccccaggctt cgccggcgg gctgaggcg    180 gccggcggc cggcggcac gccgcaactg ctcaaccagg gcggcgtgcc catcgtcaat    240
```

```
atcgtcgcgc cgaacgccgc cggcctgtcg cacaaccagt tcctcgacta caacgtcgac      300
cgccagggcc tggtcctcaa caatgcgctg caagccggcg cctcgcagct cgccggacaa      360
ctggcggcca acccgcagct gcgcggcgac gccgccagtg ccatcctcaa cgaagtgatc      420
agccgcaacg cctcggcgat caacggcccg caggaaatct tcggccaggc cgccgactac      480
atcctggcca accccaacgg catctcggtg aacggcggca gcttcatcaa cacgccccat      540
gccagcctgc tggtcggccg tccggaactg gccgacggca agctgcaggc gctgaacacc      600
aacgacgccg tcggcgccct gcagatccag ggccagggcc tgagcaaccg ggatggcagc      660
atcgccctgc tggcgccgcg agtcgacagc caaggcaaga tcgaggcgtc ggccgagctc      720
gacctgaccg tcggtcgcaa ccgcatcgac tacccgagcg gcaaggtcga gcgcgacccg      780
tccggcgacg tccgtccggg cgagcggcgc atcgacgcca gcctgttcgg cgccatgcag      840
gccggacgca tcaacatcct cagcaccgcc gagggcgccg gcgtgcgcgt cggcccggtc      900
gggatcgacg gcagggacgg cgtcgacctg cgctccgccg gcgacctgtc gatcagcggc      960
caggcgcttc ccgacaacag cctgaacgcc ttgcgcgcgg cgatccgcag cgacagcggc     1020
aacgtcggcc tgcatgcccg cggcgacctg agcctggccg ccgccgacgt cagcggcggc     1080
agggtcgacc tcaagtccgg gcgcaacctg accctgggca gcgtggaaag ccgcaacctg     1140
cgggaaagcc gcgagcgctg gagcaacagc accatcggca tcacctggga aacctacgac     1200
cgcacgcgta ccgtcaccga ttcgaagcag cacggcagcc ggatcgatgc ccgcgccgac     1260
gcgagcctgg ccgcgcgggg cgacagcgaa ctgagggcgg cgacggtcaa ggccggcgct     1320
accctgaaag tctccagcgg cggcgatacc cgtcttctcg ccgccaccga gacccgcacc     1380
gaacgcgacc agggcgcgca ccgcaagcac ctgtggaaag ccaactggga caagggcagc     1440
agcgagcaac gcagcgtggc cagcagcctc gaaggcgcgc gggtcgaact cggcggcggc     1500
cggcgcctga atctggaagg cgccgacgtg ccagccgcg gcgacctcga cctgcaagcc     1560
aagagcgtcg acatcggcag cgccagccgc agccacagca gccgcgacaa cagctactcc     1620
ggcgacctgg tcggcggcag cttcttcggc agccacggcg atggcgacag cggcaagacc     1680
ctgcaacagg gcagccgggt caaggccgac ggcgcactga cggtgaccgc cgatgcggtc     1740
gaggtgcgcg gcagccaggt acgcggcgcg cgcaaggccg aggtagtcag cgggaaaggc     1800
tcgctgcgca tcgacggcgt ggaggaaacc gcccacagca acagctacag caaggacagc     1860
aagttcttcg gcatcgccaa ggacgagagt cgccagcgca gcaaggacag cagcaaccgc     1920
gccagcgaag tacgctcgga cagcaacctg accctgcgca gcgccgccga catcgccatt     1980
cgcggctccc gggtcgaggc tggcggcgcc ctcgccgccg aggccaaggg caacctggag     2040
atagcctcgg cgcaggagcg ccacgacggc aacgacagcc gccacacccg cggcttcgac     2100
gcctatgccg gcgagcagac cccaggcagc cgccaatacc gcgccggggt cgctaccag      2160 gaccagcgga ccagcgtccg ccgcgaggaa acccgcaaca gcggctccag cctgggcggc     2220
gcctccctgg ccgtgaaggc cggcggcgat ctcaccgtga aggggccga gctgaaggcc      2280 agcgcgggcg acgccagcct ctccgggaag aacgtcgccc tgctcgccga gcaggacagc     2340
aagacccgca gcagcgaaca gaccaccacc ggcggcggct tctactatac cggcggcctg     2400
gaccgtgccg gcagcggtat cgaagtcggc caccagcgga tcgacgagaa cgacgccgaa     2460
agccatgcgc gcaccagcca ggtgaacgcg acgggcaatc tcaggatcga cgccgcccag     2520
ggcagcctga cgacgcaggg cgcgcgcctg gaggccggcg acagcctggc ggtcgccgcc     2580
```

```
ggcacggtcg acaaccaggc cgcccgcgac agccagagca gccagcgcca cgacagcggc    2640
tggagcggcg acatcggcgc caacctcgag taccgcggca tcgcccggcc gatcgagaag    2700
gcggtcgaag gcgtcgccca gcgcaaggtc caccagcccg gcctgctcga caacctggag    2760
cagccgaacg tcggcgtcga cctcgagatc agccaccgcg acagccgcgg cgagcaacag    2820
gcgagccagg cgcaggtcag cagcttcgcg ggcggccagg tcgaactgaa ggtcggcgac    2880
gccctgcggg acgagggcac ccgttaccag gctcgcagcg gaggcctcct catcgacgcc    2940
gccaggcatg acgccagggc ggcggagaac acctccggca gccatgagca gagcctcgac    3000
gccaaggtcg gcgggcgcct ctacaccacc accggccagg acctgaacct gcgcctgagc    3060
ggcattggcg gcagcagcga gaacagcgcc agccagacca ccgcggtggt cggcgaatac    3120
gccgcgaagc agggcgtcga gatccgcctc ggcggagacg gcctctacca gggcagccgc    3180
ttcgacggcg gcgaagccgg ggtcaggctc agcgccggcg gcaacctggc cctggaacag    3240
gccaacgacc ggcagagcgc cagcagcgcc agcctgcgtg gcgacgccgc gttgagcggc    3300
ggcatggccc ccagcgccaa cggcaaaggg ctgaacgcca cgcgccggcct gcaactcgac    3360 cacaaggccg cgacagccg ggacagccag gcgcgggtcg ccgacatcca ggccaagggc    3420
gcggtggagc tgcgcagcgg cggcgatctg gtcctgcaag gcagcaatat cggcagcgcg    3480
gcagcgaaga ccggcgacat agtcctggcc gccggcggca agctcgacct gcaggccgcc    3540
cgcgatagcc accgggccgg gggaaacaac ctcggcggcg gcttcagcct aggcggcggc    3600
agcgttcgcg acgccgaaac gagcagcaag aacggcagcg tcagcggcaa cttcaacatc    3660
ggccgggtcg acgaggaacg tcacgcgctg aacggcggca acctgcacag cgcgaccaag    3720
gccagccttt ccagcgccgc agacgacgcc accgcggtac gcctgcaagg cactcgcatc    3780
gaagccgccc aggtcagcct cgaagccggc aacggcggca ttctccagga gtccgccgaa    3840
tccagcgagc ggcgcgacaa ctggggcgtg ctgctcggtg ccggggccaa cggcggcaag    3900
accaccggcg cgccgagcga ctaccggagc gactatgccg tccaggcccg cgccaaggtc    3960
gatgtcgatg tcctgcgcag ccagacccag ggcgacagcg tcatccaggc cgaccgggta    4020
atcctggcga gccagggcga caccgcctg gaggcgcgc gcatcgacgc ggcacaggtg    4080
gacgggcgca tcggcggcga cctgcgggtg gagagccgcc aggaccgcgc ggagggcgtg    4140
aaggtcaacg tcgacgcgcg cctgggcgtg gagaagaacc agcccggcct ggtgaacaag    4200
ctggcgagca agaccggacc gttgaaggac aagctggaaa ccaaggccga gaatgctttc    4260
gacaagcacc gcggcaagtt ggagaacggc atcgaccgta atgtcgagcg gctcggcaag    4320
gccggggaca acctcctcgc caaagccgaa aaggccaagg agcgcctggg cgagaagctg    4380
gtccgcagcg gcagctacga ggtcaacccg gagccgcgcg cgccttcgc cagcaagctg    4440 gacagggcca ggggctatct ggcggagaaa ggcgaagcgc tcggcgaccg gctgtccggc    4500
ctcaagcagc gcctgtcgcc gaacaagacc ggtagctatg tggtgaacga caagcagacg    4560
gccggcgcca aggtcggcaa tgccgccgag aacgtgctgt cggcgacaa gagcggcgaa    4620 gcctcggtaa ccccgacgct gtacctggac gtcagccacg tcagccgcaa ctacgtcacc    4680
gaggcctccg gcatcaccgg caggcagggc gtgaacctgc aggtgggcgc agcgacccag    4740
ctgaccggcg cacggatcag cgccagcgac ggcaaggtcg acctcggcgg ctcgcgcgtg    4800
gaaacccgcg ccctggccgg caaggactac cgcgccgatc tcggcctgaa cgtctccagg    4860
tcgccggtgg acctggcctt cggtatcaag gacgagttca gccaggagca cgaccaggcg    4920
acccgcgacg accaggcctt caacctcggc gccctgcgcg tcggcggacg caaccgcgac    4980
```
cagcagttgc aggccggcat cgagcagaag gccgactaa                          5019

<210> SEQ ID NO 11
<211> LENGTH: 711
<212> TYPE: DNA
<213> ORGANISM: Artificial Sequence
<220> FEATURE:
<223> OTHER INFORMATION: Nhe with pelB leader sequence

<400> SEQUENCE: 11
atgaaatacc tgctgccgac cgctgctgct ggtctgctgc tcctcgctgc ccagccggcg    60
atggccaata cttatgtaag gaaccagtt aatgcattta ctcacttagg tggagcgata   120
ttatcattta ttgcgttatt agctatgctt gtgaaagttt ctatcaagat gccatcattt   180
gctgcaatta cagctgttat tttgtttggt attggaatga tggtccttta tacgcgtca   240
gctgtatatc atagtgttgt ggccaatgaa cgtgttatat acttctttag gaagctagat   300
cattctatga tttttatatt aattgcaggt acatatgcac ccttttgctt aattacatta   360
aattcagcaa gtggtttgct attattttgt ttagtctatg caactgcgat tgtggcatt    420
gtatttaaaa tgttttggtt taattgtcca aggtggttat cgacagcaat ttatattacg   480
atgggttggt taattgtttt attctttgca ccgttagctg agaatttaag tacaggaggc   540
attattttct tagtacttgg tggcattttt tatacaattg gtggatttat ttatggaaca   600
aagccaaaat ggttagagtt taaatatatg gggcatcatg aaattttca tgtttttgta   660
ttattaggta gtcttgcgca ttttctaagt gtatattgtt acgtaattta a            711

<210> SEQ ID NO 12
<211> LENGTH: 2220
<212> TYPE: DNA
<213> ORGANISM: Artificial Sequence
<220> FEATURE:
<223> OTHER INFORMATION: hlyA of Vibrio cholera with pelB leader
      sequence

<400> SEQUENCE: 12
atgaaatacc tgctgccgac cgctgctgct ggtctgctgc tcctcgctgc ccagccggcg    60
atggccgcaa atatcaatga accaagtggt gaagcggcgg atattattag tcaagtcgct 120
gatagtcatg caataaaata ttacaatgct gctgattggc aagccgaaga caacgcatta 180
ccgagcttag ctgagctgcg cgatttggtg attaaccagc aaaaacgcgt tttggttgat 240
ttcagtcaga tcagtgatgc tgaaggtcaa gcagagatgc aagcccaatt cagaaaggct 300
tatggggtgg gttttgctaa tcaatttatt gtcatcactg aacataaagg ggaactgctg 360
tttacacctt ttgatcaggc agaagaggtt gaccctcaat tactcgaagc gccgcgtacc 420
gctcgcttat tagcgcgctc tggttttgca agtccggcac cggcaaacag cgaaacaaat 480
accttgccgc atgtggcttt ttacatcagt gtcaaccgtg cgatcagcga tgaagagtgt 540
acctttaaca actcttggtt gtggaaaaac gaaaagggca gtcgtccgtt ctgtaaagat 600
gccaatatct cattgattta tcgagttaac ctagagcgtt cattgcaata cggcattgtg 660
ggttccgcga caccggatgc caaaattgtg cgtatcagcc tagatgatga cagcacggga 720
gccggcattc atctgaatga tcaactcggt tatcgtcagt ttggagccag ttatacgacg 780
ttagatgcct atttccgtga gtggtcaacc gatgcgattg cccaagatta tcgcttcgtg 840
tttaacgcat cgaacaataa agcgcagatc ctgaaaacct ttcctgtcga taacattaac 900
gagaaatttg agcgcaaaga ggtttcaggt tttgagcttg ggtgactgg tggggtggaa 960

```
gtcagtggag atggcccgaa agccaaacta gaggcgagag caagttatac ccagagtcgc    1020
tggttaacct acaacacaca agactatcgt attgagcgta atgcgaagaa tgcgcaagcg    1080
gttagcttta catggaatcg tcaacaatac gcgacagcag aatcgctact caatcgttcg    1140
accgatgctt tgtgggtgaa tacctacccg gtagatgtaa accgtattag cccgctgagc    1200
tacgcgagtt ttgtgccgaa aatggatgtg atttataaag cctcagccac agagacaggc    1260
agtacggatt ttatcatcga ctcttcggtc aatatccgcc caatctataa cggtgcttat    1320
aagcactact atgtggtcgg tgctcatcag ttctaccatg gctttgaaga taccccacgt    1380
cgtcgaatca cgaaatcggc aagctttacg gtcgattggg atcacccagt attcacgggt    1440
ggccgcccgg tcaacctaca acttgccagc tttaacaacc gctgtattca agtcgatgct    1500
caaggtcgct tggcggccaa tacgtgcgat agccagcaat cagcgcaatc gttcatctat    1560
gatcagcttg gtcgttatgt gagtgcgagt aacaccaagc tctgtcttga tggtgaggca    1620
ttagacgcat tgcaaccctg taaccaaaac ctgactcagc gttgggagtg gcgtaaaggc    1680
acagatgaat tgaccaatgt ctacagcggc gagtcccttg acatgacaa acaaaccggt    1740 gagcttggtt tgtatgcgag cagcaacgat gcggtaagtt tacgtaccat caccgcttat    1800
accgatgtgt ttaatgcgca agaaagttcg ccgattctgg gttacacaca agggaaaatg    1860
aatcagcagc gtgtgggaca agatcatcgt ttgtatgtgc gagcgggtgc tgccattgat    1920
gcattagggt ccgcctccga tttattggtt ggtggcaatg tggtagctt gagttcggtg    1980 gatctgtccg gcgtgaaatc catcacggca acctctggtg atttccaata tggcggtcag    2040
cagttggtgg cgctgacatt cacctaccaa gatggacgtc agcaaacggt aggctcgaaa    2100
gcgtatgtca ccaatgctca tgaagaccgt ttcgatttac cggctgccgc taagatcact    2160
caactgaaaa tttggtctga cgattggttg gtgaaagggg ttcaatttga tttgaactaa    2220
```

<210> SEQ ID NO 13
<211> LENGTH: 7410
<212> TYPE: DNA
<213> ORGANISM: Artificial Sequence
<220> FEATURE:
<223> OTHER INFORMATION: hlyBACD operon of E. coli

<400> SEQUENCE: 13

```
ttggtttgct ttttttacc tgccaccgca atgaatgctt ttttatgtt aatgtgcgtt      60 atgaaactaa atgcaagaaa catatttaaa ggattaatat cgttctctca cagactccgt     120
ttacttattc aagaatataa tttaatttat agtgagctta ttatgaatat gaacaatcca     180
ttagaggttc ttgggcatgt atcctggctc tgggccagtt ccccattaca cagaaactgg     240
ccagtctctt tgtttgcaat aaatgtatta cctgcaatac gggctaacca atatgcttta     300
ttaacccggg ataattaccc tgttgcatat tgtagttggg ctaatttaag tttagaaaat     360
gaaattaaat atcttaatga tgttacctca ttagtcgcag aagactggac ttcaggtgat     420
cgtaaatggt tcattgactg gattgctcct tcggggata acggtgccct gtacaaatat     480
atgcgaaaaa aattccctga tgaactattc cgagccatca gggtggatcc caaaactcat     540
gttggtaaag tatcagaatt tcacggaggt aaaattgata aacagttagc gaataaaatt     600
tttaaacaat attaccacga gttaataact gaagtaaaaa acaagacaga tttcaatttt     660
tcattaacag gttaagagat aattaaatgc caacaataac cactgcacaa attaaaagca     720
cactacagtc tgcaaagcaa tcctctgcaa ataaattgca ctcagcagga caaagcacga     780
```

```
aagatgcatt aaaaaagca gcagagcaaa cccgcaatgc gggaaacaga ctcattttac    840
ttatccctaa agattataaa ggacagggtt caagccttaa tgaccttgtc aggacggcag    900
atgaactggg aattgaagtc cagtatgatg aaaagaatgg cacggcgatt actaaacagg    960
tattcggcac agcagagaaa ctcattggcc tcaccgaacg gggagtgact atctttgcac   1020
cacaattaga caaattactg caaaagtatc aaaaagcggg taataaatta ggcggcagtg   1080
ctgaaaatat aggtgataac ttaggaaagg caggcagtgt actgtcaacg tttcaaaatt   1140
ttctgggtac tgcactttcc tcaatgaaaa tagacgaact gataaagaga caaaaatctg   1200
gtagcaatgt cagttcttct gaactggcaa aagcgagtat tgagctaatc aaccaactcg   1260
tggacacagc tgccagcatt aataataatg ttaactcatt ttctcaacaa ctcaataagc   1320
tgggaagtgt attatccaat acaaagcacc tgaccggtgt tggtaataag ttacagaatt   1380
tacctaaccT tgataatatc ggtgcagggt tagatactgt atcgggtatt ttatctgcga   1440
tttcagcaag cttcattctg agcaatgcag atgcagatac cggaactaaa gctgcagcag   1500
gtgttgaatt aacaacgaaa gtactgggta atgttggaaa aggtatttct caatatatta   1560
tcgcacagcg cgctgcacag ggattatcta catctgctgc tgctgccggt ttaattgctt   1620
ctgtagtgac attagcaatt agtcccctct cattcctgtc cattgccgat aagtttaaac   1680
gtgccaataa aatagaggag tattcacaac gattcaaaaa acttggatac gatggtgaca   1740
gtttacttgc tgcttttcac aaagaaacag gagctattga tgcatcgtta acaacgataa   1800
gcactgttct ggcttcagta tcttcaggta ttagtgctgc tgcaacgaca tctctggttg   1860
gtgcaccggt aagcgcgctg gtaggggctg ttacgggat aatttcaggc atccttgagg   1920
cttcaaaaca ggcaatgttt gaacatgtcg ccagtaaaat ggccgatgtt attgctgaat   1980
gggagaaaaa acacggcaaa aattactttg aaaatggata tgatgcccgc catgctgcat   2040
ttttagaaga taactttaaa atattatctc agtataataa agagtattct gttgaaagat   2100
cagtcctcat tacccagcaa cattgggata cgctgatagg tgagttagcg ggtgtcacca   2160
gaaatggaga caaaacactc agtggtaaaa gttatattga ctattatgaa gaaggaaaac   2220
gtctggagaa aaaaccggat gaattccaga agcaagtctt tgacccattg aaaggaaata   2280
ttgacctttc tgacagcaaa tcttctacgt tattgaaatt tgttacgcca ttgttaactc   2340
ccggtgagga aattcgtgaa aggaggcagt ccggaaaata tgaatatatt accgagttat   2400
tagtcaaggg tgttgataaa tggacggtga aggggggttca ggacaagggg tctgtatatg   2460
attactctaa cctgattcag catgcatcag tcggtaataa ccagtatcgg gaaattcgta   2520
ttgagtcaca cctgggagac ggggatgata aggtcttttt atctgccggc tcagccaata   2580
tctacgcagg taaaggacat gatgttgttt attatgataa aacagacacc ggttatctga   2640
ccattgatgg cacaaaagca accgaagcgg gtaattacac ggtaacacgt gtacttggtg   2700
gtgatgttaa gattttacag gaagttgtga aggagcagga ggtttcagtt ggaaaaagaa   2760
ctgaaaaaac gcaatatcgg agttatgaat tcactcatat caatggtaaa aatttaacag   2820
agactgataa cttatattcc gtggaagaac ttattgggac cacgcgtgcc gacaagttt   2880 ttggcagtaa atttactgat atcttccatg gcgcggatgg tgatgaccat atagaaggaa   2940
atgatgggaa tgaccgctta tatggtgata aaggtaatga tacgctgagg ggcggaaacg   3000
gggatgacca gctctatggc ggtgatggca atgataagtt aattgggggg acaggtaata   3060
attaccttaa cggcggtgac ggagatgatg agcttcaggt tcaggggaat tctcttgcta   3120
aaaatgtatt atccggtgga aaaggtaatg acaagttgta cggcagtgag ggagcagatc   3180
```

```
tgcttgatgg cggagaaggg aatgatcttc tgaaaggtgg atatggtaat gatatttatc   3240
gttatctttc aggatatggc catcatatta ttgacgatga tgggggaaa gacgataaac    3300 tcagtttggc tgatattgat ttccgggatg tggccttcag gcgagaaggt aatgacctca   3360
tcatgtataa agctgaaggt aatgttcttt ccattggtca taaaaatggt attacattca   3420
ggaactggtt tgaaaagag tcaggtgata tctctaatca ccagatagag cagattttg     3480 ataaagacgg cagggtaatc acaccagatt cccttaaaaa ggcacttgag tatcaacaga   3540
gtaataataa ggcaagttat gtgtatggga atgatgcatt agcctatgga agtcaggata   3600
atcttaatcc attaattaat gaaatcagca aaatcatttc agctgcaggt aattttgatg   3660
ttaaagagga aagagctgca gcttctttat tgcagttgtc cggtaatgcc agtgattttt   3720
catatggacg gaactcaata actttgacag catcagcata atttattaat ttaaataata   3780
gcaatcttac tgggctgtgc cacataagat tgctattttt ttggagtcat aatggattct   3840
tgtcataaaa ttgattatgg gttatacgcc ctggagattt tagcccaata ccataacgtc   3900
tctgttaacc cggaagaaat taaacataga tttgacacag acgggactgg tctgggatta   3960
acgtcatggt tgcttgctgc gaaatcttta gaactaaagg taaaacaggt aaaaaaaaca   4020
attgaccgat taaactttat ttcttttgccc gcattagtct ggagagagga tggacgtcat   4080
tttattctga ctaaagtcag taaagaagca aacagatatc ttattttga tctggagcaa   4140 cgaaatcccc gtgttctcga acagtctgag tttgaggcgt tatatcaggg gcatattatt   4200
cttattgctt cccgttcttc tgttaccggg aaactggcaa aatttgactt tacctggttt   4260
atccctgcca ttataaaata cagaaaaata tttattgaaa cccttgttgt atctgttttt   4320
ttacaattat ttgcattaat aaccccccctt ttttttcagg tggttatgga caaagtatta   4380
gtacacaggg ggttttcaac ccttaatgtt attactgtcg cattatctgt tgtggtggtg   4440
tttgagatta tactcagcgg tttaagaact tacattttg cacatagtac aagtcggatt    4500
gatgttgagt tgggtgccaa actcttccgg catttactgg cgctaccgat ctcttatttt   4560
gagagtcgtc gtgttggtga tactgttgcc agggtaagag aattagacca gatccgtaat   4620
tttctgacag gacaggcatt aacatctgtt ctggacttat tattttcatt catatttttt   4680
gcggtaatgt ggtattacag cccaaagctt actctggtga tcttattttc gctgccctgt   4740
tatgctgcat ggtctgtttt tattagcccc attttgcgac gtcgccttga tgataagttt   4800
tcacggaatg cggataatca atcttttcctg gtggaatcag tcacggcgat taacactata   4860
aaagctatgc cagtctcacc tcagatgacg aacatatggg acaaacaatt ggcaggatat   4920
gttgctgcag gctttaaagt gacagtatta gccaccattg gtcaacaagg aatacagtta   4980
atacaaaaga ctgttatgat catcaacctg tggttgggag cacacctggt tatttccggg   5040
gatttaagta ttggtcagtt aattgctttt aatatgcttg ctggtcagat tgttgcaccg   5100
gttattcgcc ttgcacaaat ctggcaggat ttccagcagg ttggtatatc agttacccgc   5160
cttggtgatg tgcttaactc tccaactgaa agttatcatg ggaaactggc attaccggaa   5220
attaatggta atatcacttt tcgtaatatc cggtttcgct ataagcctga ctctccggtt   5280
attttagata atatcaatct cagtattaag caggggagg ttattggtat tgtcggacgt    5340
tctggttcag gaaaaagcac attaactaaa ttaattcaac gttttatatt tcctgaaaat   5400
ggccaggtct taattgatgg acatgatctt gcgttggccg atcctaactg gttacgtcgt   5460
caggtggggg ttgtgttgca ggacaatgtg ctgcttaatc gcagtattat tgataatatc   5520
```

```
tcactggcta atcctggtat gtccgtcgaa aaagttattt atgcagcgaa attagcaggc    5580
gctcatgatt ttatttctga attgcgtgag gggtataaca ccattgtcgg ggaacagggg    5640
gcaggattat ccggaggtca acgtcaacgc atcgcaattg caagggcgct ggtgaacaac    5700
cctaaaatac ttatttttga tgaagcaacc agtgctctgg attatgagtc ggagcatatc    5760
atcatgcgca atatgcacaa aatatgtaag ggcagaacgg ttataatcat tgctcatcgt    5820
ctgtctacag taaaaaatgc agaccgcatt attgtcatgg aaaaagggaa aattgttgaa    5880
cagggtaaac ataaggaact gctttctgaa ccggaaagtt tatacagtta cttatatcag    5940
ttacagtcag actaacagaa agaacagaag aatatgaaaa catggttaat ggggttcagc    6000
gagttcctgt tgcgctataa acttgtctgg agtgaaacat ggaaaatccg gaagcaatta    6060
gatactccgg tacgtgaaaa ggacgaaaat gaattcttac ccgctcatct ggaattaatt    6120
gaaacgccgg tatccagacg gccgcgtctg gttgcttatt ttattatggg gtttctggtt    6180
attgctgtca ttttatctgt tttaggtcag gtggaaattg ttgccactgc aaatgggaaa    6240
ttaacactaa gtgggcgcag caaagaaatt aaacctattg aaaactcaat agttaaagaa    6300
attatcgtaa aagaaggaga gtcagtccgg aaaggggatg tgttattaaa gcttacagca    6360
ctgggagctg aagctgatac gttaaaaaca cagtcatcac tgttacagac caggctggaa    6420
caaactcggt atcaaattct gagcaggtca attgaattaa ataaactacc tgaactgaag    6480
cttcctgatg agccttattt tcagaatgta tctgaagagg aagtactgcg tttaacttct    6540
ttgataaaag aacagttttc cacatggcaa aatcagaagt atcaaaaaga actgaatctg    6600
gataagaaaa gagcagagcg attaacaata cttgcccgta taaaccgtta tgaaaattta    6660
tcgagagttg aaaaaagccg tctggatgat ttcaggagtt tattgcataa acaggcaatt    6720
gcaaaacatg ctgtacttga gcaggagaat aaatatgtcg aggcagcaaa tgaattacgg    6780
gtttataaat cgcaactgga gcaaattgag agtgagatat tgtctgcaaa agaagaatat    6840
cagcttgtca cgcagctttt taaaaatgaa attttagaca agctaagaca aacaacagac    6900
aacattgagt tattaactct ggagttagag aaaaatgaag agcgtcaaca ggcttcagta    6960
atcagggccc ctgtttcggg aaaagttcag caactgaagg ttcatactga aggtggggtt    7020
gttacaacag cggaaacact gatggtcatc gttccggaag atgacacgct ggaggttact    7080
gctctggtac aaaataaaga tattggtttt attaacgtcg ggcagaatgc catcattaaa    7140
gtggaggcct ttccttacac ccgatatggt tatctggtgg gtaaggtgaa aaatataaat    7200
ttagatgcaa tagaagacca gaaactggga ctcgttttta atgtcattgt ttctgttgaa    7260
gagaatgatt tgtcaaccgg gaataagcac attccattaa gctcgggtat ggctgtcact    7320
gcagaaataa agactggaat gcgaagcgta atcagctatc ttcttagtcc tctggaagag    7380
tctgtaacag aaagtttaca tgagcgttaa                                     7410
```

BACTERIA FOR TARGETING TUMORS AND TREATING CANCER

FIELD OF THE INVENTION

The present invention relates to bacteria, a drug delivery composition, and methods of using the same for uses such as treating cancer.

BACKGROUND

Most antitumor drugs act against all actively dividing cells, resulting in serious or even lethal side effects. Targeted therapy has to be able to discriminate tumor from non-tumor tissues when systemically administered, so that both primary and disseminated tumors are treated.

Previous targeted therapy has relied on abiotic drugs. When systemically delivered, the abiotic drugs are dramatically diluted in the bloodstream, with only a small fraction being available for tumors. Moreover, the abiotic drugs depend on tumor vasculature for delivery and thus cannot effectively diffuse to poorly vascularized and hypoxic tumor tissues. Therefore, a variety of obligate or facultative anaerobes that are capable of post-delivery reproduction and prefer poorly vascularized rumor tissues, have been evaluated for their safety and efficacy in targeting tumors over the last decades. However, despite the increasing attention towards the bacterial therapy of cancers, its anticancer efficacy has so far been unsatisfactory.

In view of the demand for increasing the anticancer efficacy, more treatment methods and therapeutic agents that target tumors more specifically and kill tumors effectively are desired.

SUMMARY

One example embodiment of the present invention provides a series of bacteria for targeting tumors and treating cancer. Each of the bacteria includes a nucleic acid system and a gene encoding a cytotoxin which kills tumor cells but does not affect viability of the bacterium. The nucleic acid system includes a first DNA fragment encoding a toxin which kills the bacterium, a second DNA fragment encoding an antidote which negates the toxin, a promoter of an antidote gene, and a constitutive promoter of a toxin gene.

In some embodiments, the gene encoding the cytotoxin is a homologous gene. In some embodiments, the gene encoding the cytotoxin is a heterologous gene. In some embodiments, the bacterium for targeting tumors and treating cancer is a genetically modified bacterium.

In some embodiments, the bacterium includes a constitutive promoter of a cytotoxin. In some embodiments, the bacterium includes an inducible promoter of a cytotoxin such that the cytotoxin are expressed in tumor tissues but silenced in non-tumor tissues. In some embodiments, the bacterium includes a repressible promoter of a cytotoxin such that the cytotoxin are repressed in non-tumor tissues but expressed in tumor tissues.

In some embodiments, the second DNA fragment is transcribed at tumor tissues but not transcribed at non-tumor tissues. The promoter of the antidote gene operably linked to the second DNA fragment, represses transcription of the second DNA fragment under control of a glucose level such that the antidote is expressed at the tumor tissues but not expressed at the non-tumor tissues. The constitutive promoter of the toxin gene operably linked to the first DNA fragment, causes constitutive transcription of the first DNA fragment such that the toxin is expressed at the tumor tissues and the non-tumor tissues.

In some embodiments, the promoter of the antidote gene controls transcription of the antidote gene such that glucose represses the transcription of the antidote gene. In some embodiments, the constitutive promoter of the toxin gene causes constitutive expression of the toxin gene.

In some embodiments, the first DNA fragment is transcribed at non-tumor tissues but not transcribed at tumor tissues. The constitutive promoter of the antidote gene operably linked to the second DNA fragment, causes constitutive transcription of the second DNA fragment. The promoter of the toxin gene operably linked to the first DNA fragment, causes transcription of the first DNA fragment under control of a glucose level. Expression of the toxin is higher than constitutive expression of the antidote under the control of the glucose level such that the toxin kills the bacterium at the non-tumor tissues.

In some embodiments, the promoter of the toxin gene controls transcription of the toxin gene such that glucose induces the transcription of the toxin gene. In some embodiments, the constitutive promoter of the antidote gene causes constitutive expression of the antidote gene.

In some embodiments, the bacterium for targeting tumors and treating cancer grows at tumor tissues but does not grow at non-tumor tissues.

Another example embodiment provides a drug delivery composition which includes the bacterium for targeting tumors and treating cancer. Another example embodiment provides a method of treating cancer by administering the bacterium or the drug delivery composition.

In some embodiments, the cytotoxin is selected from a group consisting of *Pseudomonas aeruginosa* exolysin, *Bacillus cereus* non-hemolytic enterotoxin, *Vibrio cholera* hemolysin A and *Escherichia coli* alpha-hemolysin.

Another example embodiment relates to introducing a heterologous gene into a tumor-targeting bacterium or causing a tumor-targeting bacterium to overexpress a homologous gene. The heterologous or homologous gene encodes a cytotoxin that kills tumor cells. In some embodiments, the cytotoxin encoded by a heterologous gene is selected from a group consisting of *Pseudomonas aeruginosa* exolysin, *Bacillus cereus* non-hemolytic enterotoxin, *Vibrio cholera* hemolysin A; and the cytotoxin encoded by a homologous gene is *Escherichia coli* alpha-hemolysin. Examples of tumor-targeting bacteria include, but not limited to bacteria that selectively colonize solid tumors and leave non-tumor tissues intact by sensing signals of tumor microenvironment, such as hypoxia, glucose deprivation and acidification, and accordingly control their own viability. These tumor-targeting bacteria may be natural or genetically modified bacteria.

Other example embodiments are discussed herein.

BRIEF DESCRIPTION OF THE DRAWINGS

FIG. 6A shows the inhibitory effect of intravenously injected E. coli JYH1 on the growth of HCT 116 tumors in nude mice in accordance with an example embodiment.

FIG. 6B shows the inhibitory effect of intravenously injected E. coli JYH1 on the growth of SW480 tumors in nude mice in accordance with an example embodiment.

DETAILED DESCRIPTION

Figure 1A:
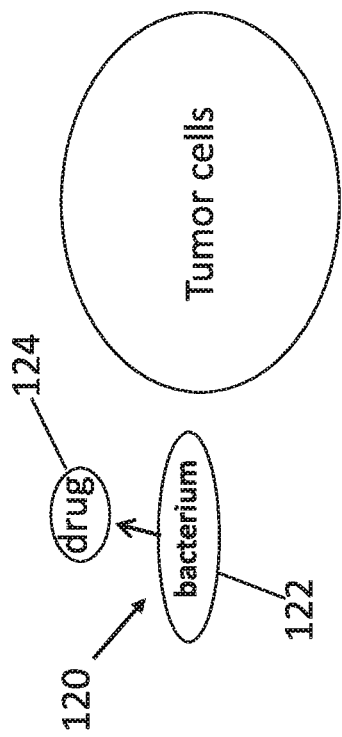
FIG. 1A shows a toxin-antidote genetic system that targets a bacterium to low-glucose environments in accordance with an example embodiment.

Example embodiments relate to a nucleic acid system. The nucleic acid system is introduced into a bacterial strain so that a genetically engineered bacterial strain targets solid tumors but leaves normal tissues intact. The genetically engineered bacterial strain grows at tumor tissues but die at non-tumor tissues.

Other example embodiments relate to a bacterium for targeting tumors and treating cancer. The bacterium includes a heterologous or homologous gene encoding a cytotoxin which kills tumor cells, and the nucleic acid system. It shall be understood that the genetic modifications made to create the bacterium for targeting tumors and treating cancer can be done in any order. For example, insertion of the nucleic acid system into the bacterium can be performed first, followed by insertion of the cytotoxin-encoding gene to kill tumor cells. Alternatively, insertion of the heterologous or homologous gene that encodes the cytotoxin that kills tumor cells can be performed first, followed by insertion of the nucleic acid system.

The cytotoxin cannot be expressed at non-tumor tissues because the bacterium does not survive or live at the non-tumor tissues. In some embodiments, the bacterium grows at tumor tissues but does not grows at non-tumor tissues.

Hypoxia is the most commonly utilized feature of tumor microenvironments for targeting bacteria to solid tumors. Obligate anaerobes that strictly target hypoxia, however, are confined to necrotic regions of solid tumors, whereas facultative anaerobes colonize throughout solid tumors but infect normal tissues due to its loose control of hypoxia targeting. Example embodiments in accordance with the invention solve these technical problems by introducing into bacteria a nucleic acid system that improves the tumor specificity of bacteria by regulating glucose-dependent viability of the bacteria.

Bacteria can produce various cytotoxins which destroy mammalian cells in diverse mechanisms. Some cytotoxins efficiently kill most epithelial and endothelial cells. However, if a bacterium is administered to a patient, the cytotoxin expressed by the bacterium may not only damage tumor cells but also normal cells. Example embodiments solve these technical problems by introducing a cytotoxin-encoding gene into a genetically engineered bacterium or a natural bacterium with tumor specificity such that the cytotoxin only damages tumor cells, but keeps normal cells intact. Alternatively, damage of normal tissues by cytotoxins may also be avoided by inducibly expressing the cytotoxins under some inducible or repressible promoters, such as glucose-repressible promoters, so that the cytotoxins are expressed only in tumor tissues but silenced in non-tumor tissues. Further, the cytotoxin-encoding gene confers the bacterium additional ability to combat cancer.

Cytotoxins of an example embodiment include but are not limited to *Pseudomonas aeruginosa* exolysin, *Bacillus cereus* non-hemolytic enterotoxin, *Vibrio cholera* hemolysin A and *Escherichia coli* alpha-hemolysin.

Exolysin (ExIA) is a pore-forming toxin excreted by *Pseudomonas aeruginosa*. ExIA has lytic capacity on most cell types such as epithelial, endothelial and fibroblastic cells and macrophages but is poorly hemolytic. Non-hemolytic enterotoxin (Nhe) is the major toxin found in *Bacillus cereus*. Nhe induces cell lysis by triggering pore formation on the membrane of mammalian cells, induces cell cycle arrest at G0/G1 phase and provokes cell apoptosis, but does not cause hemolysis. *Vibrio cholera* hemolysin A causes cell lysis by forming pores on eukaryotic cell membrane. In contrast to ExIA and Nhe, *Vibrio cholera* hemolysin A is not only cytolytic but also hemolytic. *Escherichia coli* alpha-hemolysin is produced by uropathgenic *E. coli*. Similar to *Vibrio cholera* hemolysin A, *E. coli* alpha-hemolysin is both cytolytic and hemolytic. It is cytotoxic to not only epithelial cells but also macrophages and natural killer cells, counteracting the host defense against *E. coli*.

Another embodiment provides a method of treating cancer in a patient in need thereof comprising the steps of administering to the patient a bacterium for targeting tumors and treating cancer. In some embodiments, the expressed cytotoxin causes tumor cell lysis so as to treat the cancer. In some embodiments, the bacterium is administered in combination with one or more additional cancer therapies, such as surgery, chemotherapy, radiation therapy, targeted therapy, immunotherapy, hormone therapy, or a stem cell transplant. When a therapy is administered in combination with another, the administration can be sequential or can be co-administered. In one embodiment, the cancer is melanoma.

Another embodiment provides a method of lysing tumor cells comprising the steps of contacting a bacterium which targets tumors and treats cancer with a tumor cell. In some embodiments, the method is an in vitro method. In other embodiments, the method is an in vivo method.

FIG. 1A shows a nucleic acid system 100 including a toxin-encoding gene that is constitutively expressed, and an antidote-encoding gene under the control of a glucose-repressed promoter. The nucleic acid system confers bacteria the ability to target low-glucose environments in accordance with an example embodiment.

The toxin-antidote genetic system enables bacteria to selectively grow in glucose-deprived environments but die in the presence of glucose. As glucose deprivation is a feature of solid tumor microenvironments, the bacteria equipped with the nucleic acid system can specifically target solid tumors when applied systemically. Tumor cells are commonly deprived of glucose due to fast cell growth and excessive glucose consumption as well as inadequate blood supply. A glucose concentration is 0.123-0.424 mM in tumor tissues, and a glucose concentration is 1.22-1.29 mM in normal tissues, assuming 1 g of tissues is 1 ml. The toxin-antidote nucleic acid system enables the bacteria to selectively grow under low-glucose environments.

The nucleic acid system confers the bacteria the ability to selectively grow under low-glucose condition, which is a feature of tumor microenvironment. The bacteria such as *E. coli* have the intrinsic ability of preferentially growing in solid tumors and colonizing normal tissues to a lesser extent, due to the heavily immune-suppressed microenvironment of tumors. The nucleic acid system that targets low-glucose environments confers higher tumor selectivity to the bacteria such as *E. coli* that is not sufficiently tumor specific to be used on its own, improving safety of bacterium-mediated tumor therapy.

In an example embodiment, the nucleic acid system that is a tumor-targeting system, is integrated into the chromosome of the bacteria, such that the bacteria do not solely depend on their natural ability to target tumors and in turn the safety of the bacteria is improved. In an example embodiment, the nucleic acid system is inserted into a plasmid. In an example embodiment, the nucleic acid system is a glucose-sensing system or module.

In an example embodiment, the bacteria that carry the nucleic acid system strictly colonize solid tumors by targeting low-glucose environments.

In an example embodiment, the nucleic acid system includes a toxin-encoding gene, an antidote-encoding gene, a glucose-repressed promoter that controls the transcription of the antidote-encoding gene, and a constitutive promoter that causes constitutive expression of the toxin-encoding gene.

In an example embodiment, in environments with physiological levels of glucose, the toxin is constitutively expressed whereas the antidote expression is repressed by glucose under the control of the glucose-repressed promoter. The bacteria that carry the nucleic acid system do not grow in environments with physiological levels of glucose because the antidote is not expressed to neutralize the toxin. In low-glucose environments, both the toxin and the antidote are expressed. The bacteria that carry the nucleic acid system grow in low-glucose environments because the antidote neutralizes the toxin.

In an example embodiment, the nucleic acid system includes a toxin-encoding gene, an antidote-encoding gene, a glucose-induced promoter that controls the transcription of the toxin-encoding gene, and a constitutive promoter that causes constitutive expression of the antidote-encoding gene.

In an example embodiment, in environments with physiological levels of glucose, the antidote is constitutively expressed whereas the toxin expression is induced by glucose under the control of the glucose-induced promoter. The bacteria that carry the nucleic acid system do not grow in environments with physiological levels of glucose because the toxin is expressed to a level higher than the expression of the antidote and thereby kills the bacteria. In low-glucose environments, the toxin is not expressed so that the bacteria live and grow.

In an example embodiment, the low-glucose environments include glucose at a concentration lower than 0.424 mM. In an example embodiment, the high-glucose environments include glucose at a concentration higher than 1.22 mM. In an example embodiment, the low-glucose environments have glucose at a concentration of 0.123-0.424 mM. In an example embodiment, the high-glucose environments have glucose at a concentration of 1.22-1.29 mM.

In an example embodiment, in solid tumors, a level of the expressed antidote is higher or equivalent to that of the expressed toxin so that the toxicity of the toxin is antagonized by the antidote.

In an example embodiment, the tumor-targeting nucleic acid system is a nucleic acid system that includes a first DNA fragment that encodes a toxin gene that expresses a toxin, a second DNA fragment that encodes an antidote gene that expresses an antidote that negates the toxin, a first promoter (i.e. a promoter of antidote gene) and a first constitutive promoter (i.e. a constitutive promoter of a toxin gene). The first constitutive promoter causes constitutive expression of the toxin gene. The first promoter regulates transcription of the second DNA fragment under the control of glucose concentration, such that the second DNA fragment is transcribed under low-glucose environments or in the absence of glucose, but not transcribed in the presence of glucose or under high-glucose environments. In an example embodiment, the second DNA fragment is transcribed in the absence of glucose but not transcribed under high-glucose environments whose concentration is equal to or higher than 1 mM in M63 medium.

In an example embodiment, the first promoter (i.e. the promoter of the antidote gene) controls transcription of the antidote gene, such that glucose represses the transcription of the antidote gene. The second DNA fragment is transcribed in solid tumors but not transcribed in non-tumor tissues.

In an example embodiment, the tumor-targeting nucleic acid system is a nucleic acid system that includes a first DNA fragment that encodes a toxin gene that expresses a toxin, a second DNA fragment that encodes an antidote gene that expresses an antidote that negates the toxin, a second promoter (i.e. a promoter of a toxin gene) and a second constitutive promoter (i.e. a constitutive promoter of an antidote gene). The second constitutive promoter causes constitutive expression of the antidote gene. The second promoter regulates transcription of the first DNA fragment under the control of glucose concentration, such that the first DNA fragment is transcribed under high-glucose environments or in the presence of physiological levels of glucose, but not transcribed in the absence of glucose or under low-glucose environments. In an example embodiment, the first DNA fragment is not transcribed in the absence of glucose but transcribed under high-glucose environments whose concentration is equal to or higher than 1 mM in M63 medium.

In an example embodiment, the second promoter controls transcription of the toxin gene, such that glucose induces the transcription of the toxin gene. The first DNA fragment is transcribed in the non-tumor tissues but not transcribed in the solid tumors. In an example embodiment, the expression of the toxin is higher than the constitutive expression of the antidote at the non-tumor tissues.

In an example embodiment, the first DNA fragment is shown as SEQ ID No.1. In an example embodiment, the second DNA fragment is shown as SEQ ID No.2.

In an example embodiment, the first DNA fragment is located upstream of the second DNA fragment. In an example embodiment, the first DNA fragment is located upstream of the first promoter. In an example embodiment, the first DNA fragment is located downstream of the second DNA fragment. In an example embodiment, the second promoter is located upstream of the first DNA fragment. In an example embodiment, the first constitutive promoter is located upstream of the first DNA fragment. In an example embodiment, the second constitutive promoter is located upstream of the second DNA fragment. In an example embodiment, the first promoter is shown as SEQ ID No.3.

In an example embodiment, the nucleic acid system includes a random sequence that consists of 5-6 nucleotides, and is located immediately upstream of the second DNA fragment and downstream of the first promoter. In an example embodiment, the random sequence is GCCTT or TGTCT.

In an example embodiment, the nucleic acid system includes a random sequence that consists of 5-6 nucleotides, and is located immediately upstream of the first DNA fragment and downstream of the second promoter.

In an example embodiment, the nucleic acid system includes a random sequence that consists of 5-6 nucleotides, and replaces original or native 5-6 nucleotides of the bacteria that are located immediately upstream of the second DNA fragment.

In an example embodiment, the nucleic acid system includes a random sequence that consists of 5-6 nucleotides, and replaces original or native 5-6 nucleotides of the bacteria that are located immediately upstream of the first DNA fragment.

In an example embodiment, the nucleic acid system includes a random sequence that consists of 5-6 nucleotides, and replaces original or native 5-6 nucleotides of the first promoter. In an example embodiment, the nucleic acid system includes a random sequence that consists of 5-6 nucleotides, and replaces original or native 5-6 nucleotides of the second promoter.

In an example embodiment, the random sequence is located downstream of the first promoter. In an example embodiment, the random sequence is located immediately upstream of the second DNA fragment.

In an example embodiment, the random sequence is located downstream of the second promoter. In an example embodiment, the random sequence is located immediately upstream of the first DNA fragment.

In an example embodiment, the nucleic acid system includes a third DNA fragment that encodes a selectable marker. In an example embodiment, the marker is chloramphenicol selectable marker ($Cm^R$). In an example embodiment, the selectable marker is a chloramphenicol resistance cassette. In an example embodiment, the third DNA fragment is shown as SEQ ID No. 4.

In an example embodiment, the third DNA fragment is located downstream of the first DNA fragment and upstream of the first promoter. In an example embodiment, the third fragment is located downstream of the second DNA fragment and upstream of the second promoter.

In an example embodiment, the nucleic acid system includes SEQ ID No.1, SEQ ID No.2. SEQ ID No.3, and SEQ ID No.4. In an example embodiment, the nucleic acid system includes a constitutive promoter to drive expression of ccdB as shown in SEQ ID No. 5. In an example embodiment, the nucleic acid system includes a rrnB transcription termination region as shown in SEQ ID No. 6. In an example embodiment, the nucleic acid system is shown as SEQ ID No. 7. In an example embodiment, the nucleic acid system is shown as SEQ ID No. 8.

In an example embodiment, the nucleic acid system includes a toxin gene, an antidote gene, a first promoter that controls transcription of the antidote gene, and a constitutive promoter for the toxin gene. In an example embodiment, the nucleic acid system includes a toxin gene, an antidote gene, a second promoter that controls transcription of the toxin gene, and a constitutive promoter for the antidote gene.

In an example embodiment, the bacterial strain is a Gram-positive bacterial strain. In an example embodiment, the bacterial strain is a Gram-negative bacterial strain.

In an example embodiment, the bacterial strain is *Escherichia coli*. In an example embodiment, the bacterial strain is selected from a group consisting of *Escherichia coli* MG1655 and *Escherichia coli* SH1.

Figure 1C:
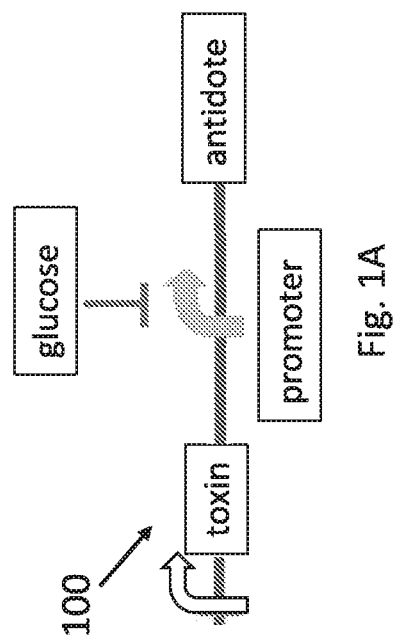
FIG. 1C shows a drug delivery composition that includes a genetically engineered bacterium that delivers anti-cancer drugs to solid tumors in accordance with an example embodiment. The anti-cancer drugs include but are not limited to anti-cancer molecules or compounds produced by the engineered bacterium.
Figure 1B:
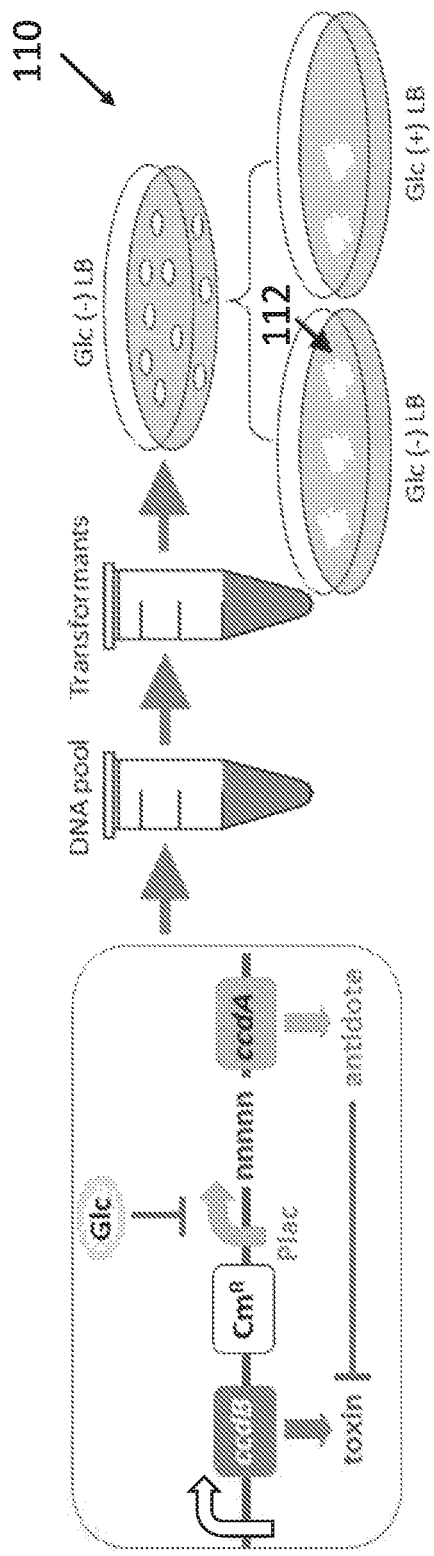
FIG. 1B shows a schematic diagram for constructing a nucleic acid system that targets *Escherichia coli* to low-glucose environments using CcdB as a toxin and CcdA as an antidote in accordance with an example embodiment.

FIG. 1B shows a schematic diagram 110 for constructing a nucleic acid system that targets *E. coli* to low-glucose environments in accordance with an example embodiment. FIG. 1B shows that a randomized, glucose-repressed lactose promoter (Plac) and a CcdA/CcdB toxin-antidote pair are employed to construct a nucleic acid system that targets *E. coli* to low-glucose environments.

CcdB is a toxin that kills host bacteria, and CcdA is an antidote to counteract CcdB. In the tumor-targeting nucleic acid system, CcdB is constitutively expressed whereas CcdA expression is repressed by glucose under the control of the glucose-repressed lactose (lac) promoter. In low-glucose environments, bacteria carrying this nucleic acid system shall grow well because the antidote CcdA is de-repressed to neutralize CcdB. In the presence of physiological levels of glucose, CcdA expression is turned off and CcdB is freed up to kill the bacteria.

In an example embodiment, in the tumor-targeting nucleic acid system, CcdA is constitutively expressed whereas CcdB expression is induced by glucose under the control of the glucose-induced promoter. In low-glucose environments, bacteria carrying this nucleic acid system shall grow well because the toxin CcdB is repressed. In the presence of physiological levels of glucose, CcdB expression is turned on to kill the bacteria.

As shown in FIG. 1B, a randomized fragment composed of 5-6 nucleotides (nnnnn) replaces the original or native 5-6 nucleotides immediately upstream of the start codon of the ccdA gene (one example of the second DNA fragment). Different sequences in this randomized fragment result in different levels of the ccdA expression. With some sequences, the glucose levels in tumors are low enough to activate the expression of CcdA to antagonize the toxicity of CcdB, and the glucose levels in normal tissues are high enough to shut down the CcdA expression under the control of the lac promoter. A selectable marker, such as chloramphenicol selectable marker ($Cm^R$) is also used in the nucleic acid system of FIG. 1B.

The nucleic acids systems with different sequences in the randomized fragment (a random library of the nucleic acid systems or DNA pool) are inserted into the chromosome of *E. coli* and the bacteria are then streaked on lysogeny broth (LB) agar plates with glucose (Glc (+)) or without glucose (Glu (−)) to screen those that fail to grow in the presence of glucose but grow in the absence of glucose. The arrow 112 indicates a clone that grows in glucose-negative medium but does not grow in medium with glucose. In an example embodiment, the concentrations of glucose on LB agar plates are 0 mM or 5 mM.

FIG. 1C shows a drug delivery composition 120 that includes a genetically engineered bacterium 122 that not only specifically targets solid tumors but also delivers to solid tumors anti-cancer drugs 124 by producing anti-cancer molecules or compounds.

The genetically engineered bacterium 122 delivers the drug 124 to solid tumors and kills the tumor cells. The genetically engineered bacterium 122 includes the nucleic acid system discussed herein, such that the bacterium grows in the solid tumors but not grow in non-tumor tissues.

The following examples are provided illustrating various embodiments.

EXAMPLE 1

Materials and Methods

Construction of a random library of engineered *E. coli* that targets low-glucose environments:

The tumor-targeting nucleic acid system designed in this example was composed of a constitutively expressed ccdB gene and a glucose-repressed ccdA gene under the control of a lac promoter. The antidote CcdA is repressed in the presence of physiological levels of glucose so that the toxin CcdB kills the bacteria. In contrast, the bacteria are alive under the low-glucose growth conditions because the expression of CcdA is de-repressed and counteracts the action of CcdB. To improve the capacity of CcdA in antagonizing CcdB under the control of the lac promoter under the low-glucose conditions or enhancing the ability of CcdB to kill bacteria in the presence of glucose, a random library of the tumor-targeting nucleic acid system was constructed by randomizing the 5 nucleotides immediately upstream of the start codon of the ccdA gene. To facilitate the genetic engineering on the chromosome by the λ-Red recombination technique, a selectable marker, chloramphenicol selectable marker ($Cm^R$), was included in the tumor-targeting nucleic acid system as illustrated in FIG. 1B.

Specifically, a set of DNA fragments (i.e. tumor-targeting nucleic acid systems) that contains the ccdB gene under the control of a constitutive promoter, a selectable marker (such as the loxP-cat-loxP cassette), a 5 nucleotides (5nt)-randomized region, and the ccdA gene under the control of a glucose-repressed promoter (such as a lac promoter) was generated by overlapping polymerase chain reaction (PCR) as shown in FIG. 1B. The 5nt-randomized region allows for generating a random library of the nucleic acid systems. The selectable marker makes it possible to insert the nucleic acid systems into the chromosome of bacteria by recombineering. Then, the library of the nucleic acid systems was inserted into the chromosome of *E. coli*, using the λ-Red recombineering technique. After 1 h-recovery in glucose-deprived LB, the bacterial culture was spread on glucose-deprived LB agar supplemented with antibiotics (12.5 μg/ml chloramphenicol if the loxP-cat-loxP cassette was used as the selectable marker). After overnight culture at 32° C., individual colonies formed on the agar. Each colony is derived from replication of a single *E. coli* that has the potential to selectively grow under low-glucose conditions. These colonies formed a random library of putative tumor-targeting bacteria. Here, the CcdB-CcdA pair could be replaced by other toxin-antidote pair.

Library Screen for Bacteria Targeting Glucose-Deprived Environment:

Glucose-deprived LB medium was used for library screen for bacteria that selectively grew under low-glucose conditions. To screen the random library, each of the clones was streaked both on the glucose-deprived LB agar and LB agar plus 5 mM glucose. After overnight culture at 37° C., clones that were found to grow readily on the glucose-deprived LB agar but not to grow on glucose-positive LB agar were further assessed using the minimal M63 medium agar. The M63 agar was supplemented with increasing concentrations of glucose in addition to 30 mM glycerol. Here, bacteria strains other than *E. coli* MG1655 could be used for screening for tumor-targeting bacteria using the same strategy.

In Vivo Assessment of the Tumor-Targeting Efficacy of Engineered Bacteria:

Six- to eight-week-old nude mice were used for tumor implantation of human cancer cell lines, and six- to eight-week-old immunocompetent BALB/c mice were used for tumor implantation of murine derived cell lines. $1 \times 10^7$ of bacteria were injected into the tail vein of each mouse. Tumor size was measured using digital calipers every three days following the bacterial injection. At the end of the experiments, mice were euthanized and their tumors and organs were removed for determination of colony forming unit. Specifically, 1 gram of tissues was homogenized in 1 ml of Phosphate-buffered saline (PBS) buffer. The resulting tissue suspensions were serially diluted and plated, and colony forming units of the diluted suspensions were counted. The number of bacteria in each tissue was calculated according to dilution ratio. Bacteria were regarded as being able to specifically target tumors if they were present in tumors but absent from organs.

In an example embodiment, the tumor-targeting nucleic acid system is composed of the constitutively expressed ccdB gene, a $Cm^R$ cassette and lac promoter-controlled ccdA with a 5nt-random sequence being located immediately upstream its start codon. These elements are not necessarily placed in the order as shown in FIG. 1B. In an example embodiment, the tumor-targeting nucleic acid system is composed of the constitutively expressed ccdA gene, a $Cm^R$ cassette and a glucose-induced promoter-controlled ccdB with a 5nt-random sequence being located immediately upstream its start codon. The ccdB-ccdA pair can be replaced by other toxin-antitoxin pair. $Cm^R$ can be replaced by other selectable markers. The number of nucleotides in the random sequence is not confined to five.

Gene Cloning:

Genes encoding cytotoxins *P. aeruginosa* ExlA, *B. cereus* Nhe, *V. hemolysin* A and *E. coli* alpha-hemolysin were synthesized and cloned in a pBAD plasmid using CloneEZ seamless cloning technology by GenScript. All the recombinant plasmids were verified by sequencing analysis.

In Vitro Cytotoxicity Assay:

Each of the cell line tested was seeded in 96-well plates at $1 \times 10^4$ cells per well in appropriate growth medium. When the cells grew to 80% confluency, they were co-cultured with *E. coli* strains tested at a moi of 100 (i.e. 100 bacteria per cell). As controls, the cells were also co-cultured with PBS alone. After 4-12 hours of incubation in antibiotic-free medium, the cells were washed thrice with PBS and stained with 1% crystal violet for 5 min. Only viable cells were stained because dead cells were removed by washing. The stained cells were gently washed with PBS and then destained with 95% ethanol. The amount of the crystal violet stain, which reflects the quantity of viable cancer cells, in the destaining solution was measured with a microtiter plate reader at 595 nm. Percentage of cells killed by the co-cultured bacteria was calculated using the formula: (control−treat)/control×100. All the experiments were performed in quadruplicate on two independent occasions.

Hemolysis Assay:

Overnight cultures of bacteria were dropped on LB agar supplemented with sheep blood and then incubated at 37° C. for 8-10 hours. Hemolysis as a result of breakdown of red blood cells was revealed by clearing of the agar.

In Vivo Assessment of Efficacy of Engineered *E. coli* on Tumors:

Six- to eight-week-old female C57BL/6N mice were used for subcutaneous tumor implantation of human or murine cancer cell lines. $10^5$-$10^6$ cells of the cell line tested were injected subcutaneously into the flank of each mouse. 10-15 days after the cell line injection when the average volume of tumors reached about 150-300 mm$^3$, $10^7$ of bacteria were injected into the tail vein of each mouse or $5 \times 10^7$ of bacteria were directly injected into each tumor. Tumor volume and body weight were measured every three days following the bacterial injection. Tumor volume was calculated with the formula (longest diameter)×(shortest diameter)$^2$×0.52. Body weight without tumor weight was calculated by subtracting estimated tumor weight from body weight (1000 mm$^3$ of tumor tissue was assumed as 1 g).

EXAMPLE 2

*E. coli* MG1655 was used in this example. The constitutively expressed CcdB, the lac promoter-controlled CcdA, the lac promoter, and $Cm^R$ were used to construct the tumor-targeting nucleic acid system. The ccdB gene was located upstream of the $Cm^R$ cassette that was located upstream of the lac promoter. A random library of the putative tumor-targeting bacteria was generated by inserting a randomized fragment (5 nucleotides in this example) in the lac promoter immediately upstream of the ccdA gene. The random library was chromosomally established in the *E. coli* strain MG1655. In this random library, each *E. coli* MG1655 variant carried in the chromosome a lac promoter variant with a distinctive 5 nucleotide-sequence in the randomized domain. The random library was screened to search for bacterial clones that selectively grew under low-glucose conditions. Specifically, the library was established on LB agar depleted for glucose. The resulting *E. coli* clones were then individually streaked on both LB agar with 5 mM glucose and LB agar without glucose to screen for those that failed to grow in the presence of glucose but grew in the absence of glucose. Approximately 1500 clones were screened and 6 clones were found to preferentially grow in glucose-negative medium.

Figure 1D:
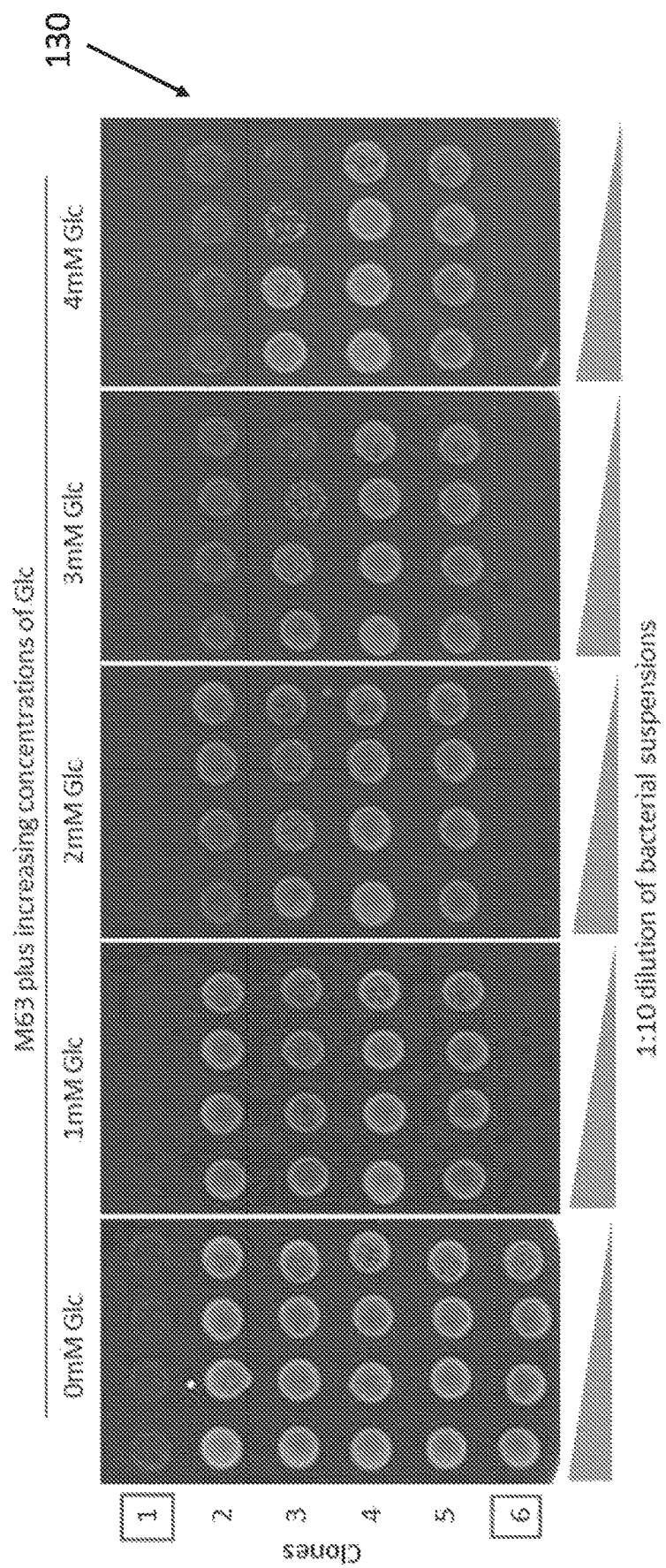
FIG. 1D shows clones that are streaked on M63 agar with different concentrations of glucose from 0 mM to 4 mM to search for those that fail to grow in the presence of glucose but glow in the absence of glucose in accordance with an example embodiment.

FIG. 1D shows drawings 130 for the sensitivity of six *E. coli* clones to glucose on minimal medium M63 agar. The 6 clones were purified, incubated overnight, and serially diluted. 10 µl of each diluted suspension was dropped on minimal medium M63 supplemented with increasing concentrations of glucose (Glu) from 0 mM Glu to 4 mM Glu to verify their phenotype. Among the 6 clones, the 1$^{st}$ and the 6$^{th}$ clones grew well on glucose-negative medium agar, but grew poorly in the presence of glucose. In the contrast, the 2$^{nd}$, 3$^{rd}$, 4$^{th}$ and 5$^{th}$ clones displayed considerable growth in both glucose-negative and glucose-positive medium agar.

Given this, the 1st and the 6th clones (boxed in FIG. 1D) were candidates of tumor-targeting bacteria and named JY1 and JY6 (also named JY8), respectively. If more library screening was carried out, more glucose-sensing clones could be identified.

The random sequence upstream of the ccdA gene in the chromosome of the clone JY1 is GCCTT. The nucleotide sequence of JY1 includes a sequence as shown in SEQ No. 5. The random sequence upstream of the ccdA gene in the chromosome of the clone JY6 is TGTCT.

The strain JY1 was deposited at the China General Microbiological Culture Collection Center (CGMCC), Institute of Microbiology, Chinese Academy of Sciences, NO.1 West Beichen Road, Chaoyang District, Beijing 100101, China under deposit no. 14577 with deposit date of 30 Aug. 2017. The strain JY6 was deposited at the CGMCC, Institute of Microbiology, Chinese Academy of Sciences, NO.1 West Beichen Road, Chaoyang District, Beijing 100101, China under deposit no. 14578 with deposit date of 30 Aug. 2017.

EXAMPLE 3

The engineered *E. coli* variants JY1 and JY6 were sensitive to glucose and failed to grow in the presence of glucose in vitro. This example provides in vivo experiments and data showing that glucose levels in tumors were low enough for JY1 and JY6 to survive and grow. JY1 and JY6 were separately injected into the tail vein of immunocompetent BALB/c mice with CT26 (a murine colorectal cancer cell line) tumors ($10^7$ cfu/mouse). The parental strain MG1655 was employed as a control. 15 days after the tail vein injection, the bacteria were analyzed for their distribution in tumor and liver. The liver was chosen for the analyses because it is more vulnerable to bacterial infection than other organs.

FIGS. 2A-2F show *E. coli* JY1 and JY6 specifically targeted tumors in mice. Error bar, SEM. *P<0.05, **P<0.01.

Figures 2A, 2B:
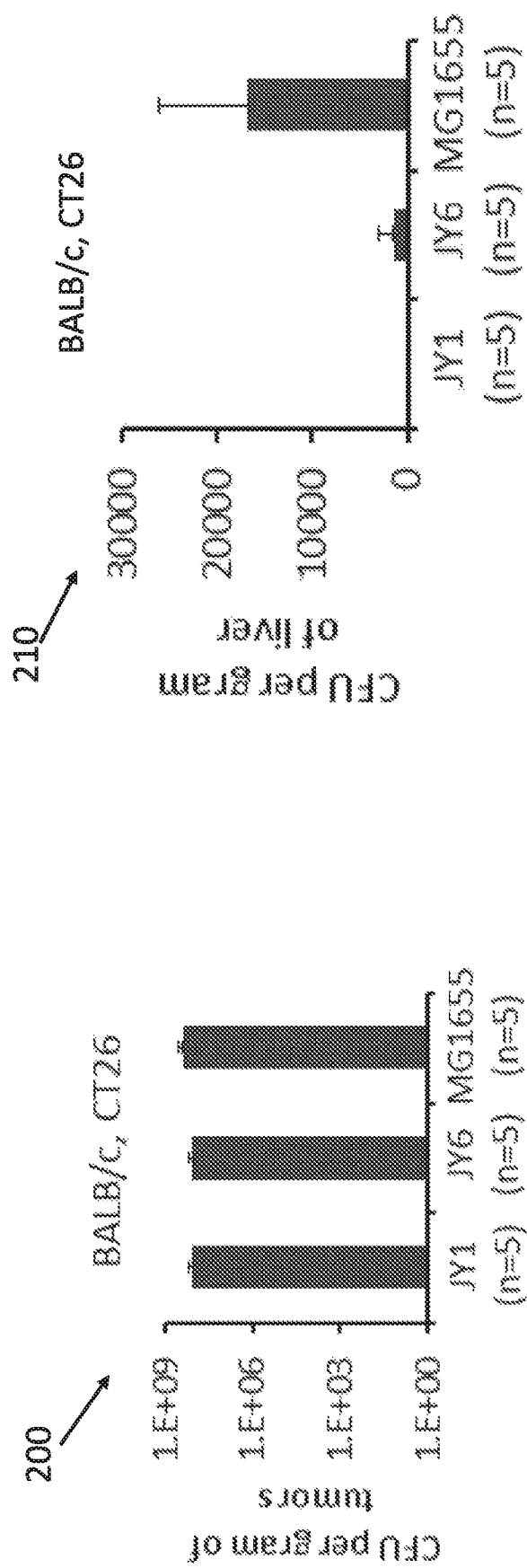
FIG. 2A shows colonization of the genetically engineered bacterial strains JY1 and JY6, and an unmodified wild-type E. coli strain named MG1655 in CT26 (a murine colorectal cancer cell line) tumors of Bagg albino/c (BALB/c) mice 15 days after intravenous injection of the bacteria ($10^7$/mouse) in accordance with an example embodiment.
FIG. 2B shows colonization of the bacterial strains JY1, JY6, and MG1655 in the liver of BALB/c mice with CT26 tumors 15 days after intravenous injection of the bacteria ($10^7$/mouse) in accordance with an example embodiment.

FIG. 2A shows colony forming unit (CFU) 200 per gram of CT26 tumors in BALB/c mice. As shown in FIG. 2A, JY1, JY6, and MG1655 comparably colonized the CT26 tumors in the BALB/c mice and their levels in the tumors were over $10^8$ cfu/g. These data showed that both JY1 and JY6 were good colonizers in the CT26 tumors carried by the immunocompetent BALB/c mice.

Figure 2D:
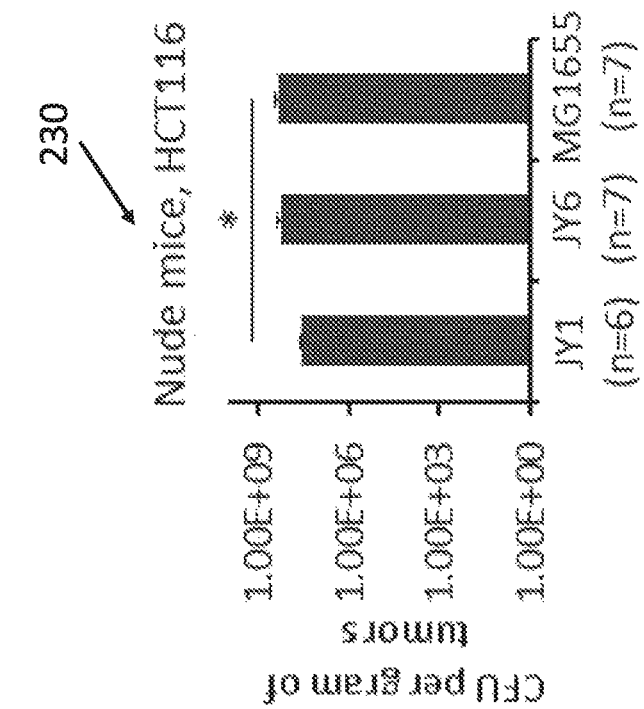
FIG. 2D shows colonization of the bacterial strains JY1, JY6, and MG1655 in tumors in nude mice with HCT116 (a human colorectal cancer cell line) tumors 7 days after intravenous injection of the bacteria ($10^7$/mouse) in accordance with an example embodiment.
Figure 2C:
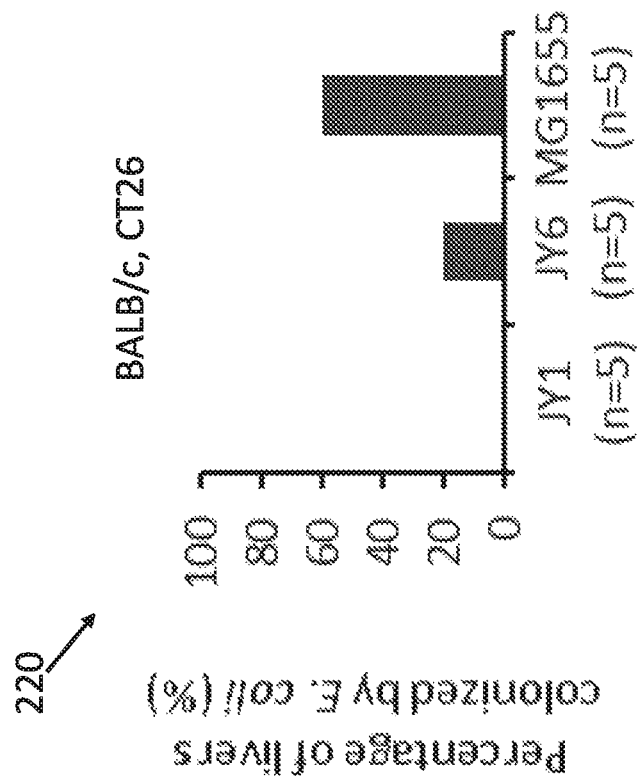
FIG. 2C shows percentage of livers colonized by the bacterial strains JY1, JY6, and MG1655 in BALB/c mice with CT26 tumors 15 days after intravenous injection of the bacteria ($10^7$/mouse) in accordance with an example embodiment.

FIG. 2B shows CFU 210 per gram of liver in BALB/c mice with CT26 tumors. As shown in FIG. 2B, JY1 did not colonize the liver of BALB/c mice with CT26 tumors. JY6 colonized the liver of BALB/c mice with CT26 to a less extent than MG1655 did. FIG. 2C shows percentages 220 of livers colonized by JY1, JY6 and MG1655 in BALB/c mice with CT26 tumors. As shown in FIG. 2C, JY6 was detected in the livers of 20% of the BALB/c mice with CT26 tumors (1 out of 5) and JY1 was not detected in the liver of any mouse, while MG1655 colonization occurred in the livers of 60% of the mice (3 out of 5). These showed that JY1 and JY6 are more specific to tumors than MG1655 and that JY1 is more specific to tumors than JY6.

Further plating analyses showed that JY1 was also absent from blood and organs including spleen, heart, lung and kidney of the immunocompetent mice. Although JY1 and JY6 displayed comparable ability to colonize the CT26 tumors, JY1 was superior in specifically targeting the tumors than JY6 in the immunocompetent mice.

Figure 2F:
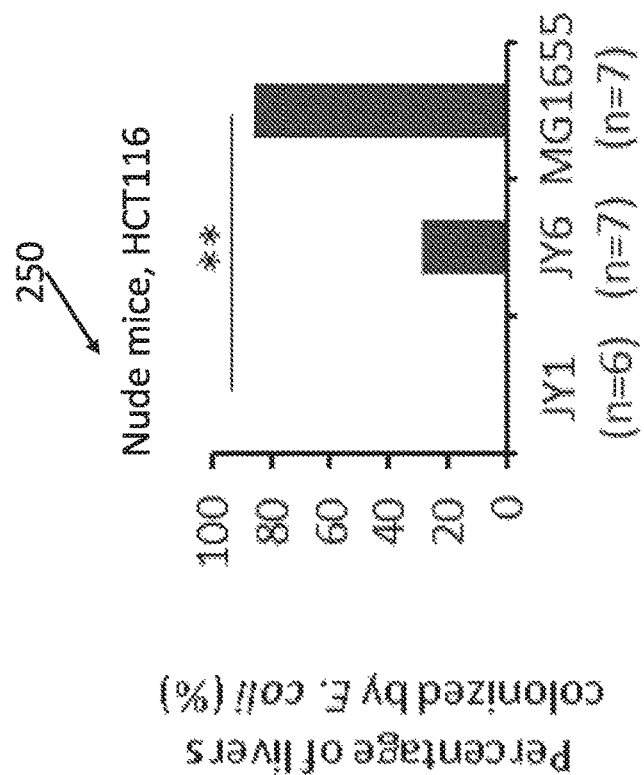
FIG. 2F shows percentage of livers colonized by the bacterial strains JY1, JY6, and MG1655 in nude mice with HCT116 tumors 7 days after intravenous injection of the bacteria ($10^7$/mouse) in accordance with an example embodiment.
Figure 2E:
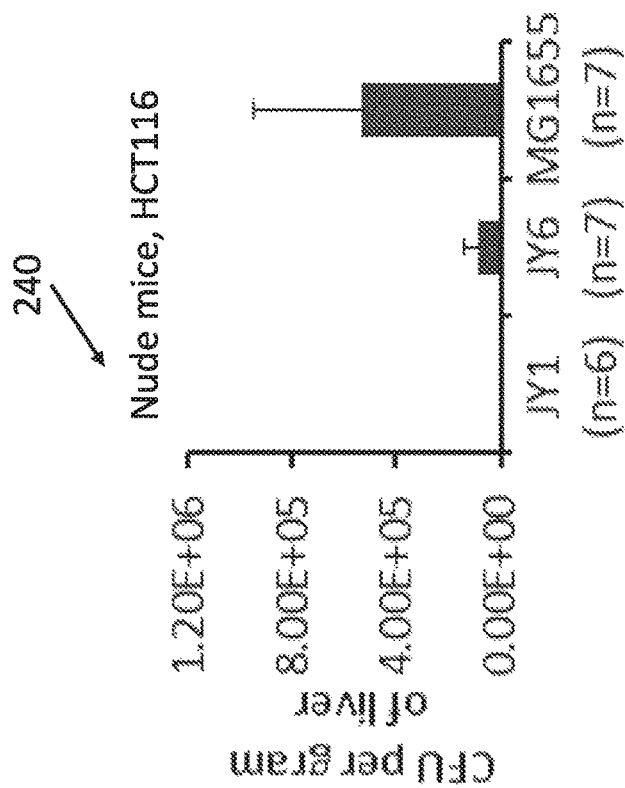
FIG. 2E shows colonization of the bacterial strains JY1, JY6, and MG1655 in the liver of nude mice with HCT116 tumors 7 days after intravenous injection of the bacteria ($10^7$/mouse) in accordance with an example embodiment.

Similar experiments were performed in immunocompromised nude mice carrying subcutaneous HCT116 (a human colorectal cancer cell line) tumors. 7 days after the tail vein injection of the bacteria ($10^7$ cfu/mouse), the bacteria were analyzed in their distribution in tumor and liver. FIG. 2D shows CFU 230 per gram of the HCT116 tumors in nude mice. As shown in FIG. 2D, JY1, JY6, and MG1655 colonized the HCT116 tumors in the nude mice. FIG. 2E shows CFU 240 per gram of liver in nude mice with HCT116 tumors. As shown in FIG. 2E, JY1 did not colonize the liver of nude mice with HCT116 tumors. JY6 colonized the liver of nude mice with HCT116 tumors to a less extent than MG1655 did. FIG. 2F shows percentage 250 of livers colonized by JY1, JY6 and MG1655 in nude mice with HCT116. As shown in FIG. 2F, JY6 and MG1655 were detected in the livers of 28.57% (2 out of 7) and 85.71% (6 out of 7) of the nude mice, respectively. Again, JY1 was not present in the liver of any mouse (n=6). These showed that JY1 and JY6 are more specific to tumors in immunocompromised mice than MG1655 and that JY1 is more specific to tumors than JY6 in immunocompromised mice.

To ensure that JY1 did not infect normal tissues, blood and homogenized suspensions of the spleen, heart, lung and kidney of each mouse in the bacteria-treated group were further examined. All these were cleared of JY1. Although JY1 avoided infecting organs, it readily colonized the HCT116 tumors and its levels in the tumors reached $3.79 \times 10^7$ cfu/g (FIG. 2D). Taken together, the in vivo data demonstrate that the tumor-targeting nucleic acid system carried by the bacteria JY1 and JY6 enables them to specifically target solid tumors in both immunocompetent and immunocompromised mice, and JY1 was superior to JY6 in the ability of targeting solid tumors.

EXAMPLE 4

The glucose-targeting nucleic acid system carried by JY1 was next grafted into the chromosome of *E. coli* SH1, to show that this nucleic acid system is not confined to a particular bacterial strain.

*E. coli* SH1 was isolated from a stool sample provided by a healthy female volunteer. The stool sample was resuspended in PBS buffer and spread on LB agar supplemented with 1 mM isopropyl 0-D-thiogalactoside (IPTG) and X-gal (0.06 mg/mi). *E. coli* formed blue colonies and were discriminated from other bacteria species. SH1 is one of the fecal *E. coli* isolates. The strain SH1 was deposited at the CGMCC, Institute of Microbiology, Chinese Academy of Sciences, NO.1 West Beichen Road, Chaoyang District, Beijing 100101, China under deposit no. 14580 with deposit date of 30 Aug. 2017.

The resulting recombinant *E. coli* strain was referred to as JYH1. The strain JYH1 was deposited at the CGMCC, Institute of Microbiology, Chinese Academy of Sciences, NO.1 West Beichen Road, Chaoyang District, Beijing 100101, China with deposit no. 14579 with deposit date of 30 Aug. 2017.

JYH1 was then intravenously injected into nude mice carrying subcutaneous SW480 (a human colorectal cancer cell line) tumors. The mice were analyzed for bacterial colonization in tumors and organs 90 days after the intravenous injection of the bacteria. Because the tumors of four JYH1-treated mice were completely cured, only two tumors in this group were available for analysis. JYH1 was detected from one of the two tumors, reaching $1.8 \times 10^8$ cfu per gram.

It shows that when the module or the nucleotide system is introduced into *E. coli* SH1, the resulting strains can not only target tumors but also treat tumors.

Figure 3B:
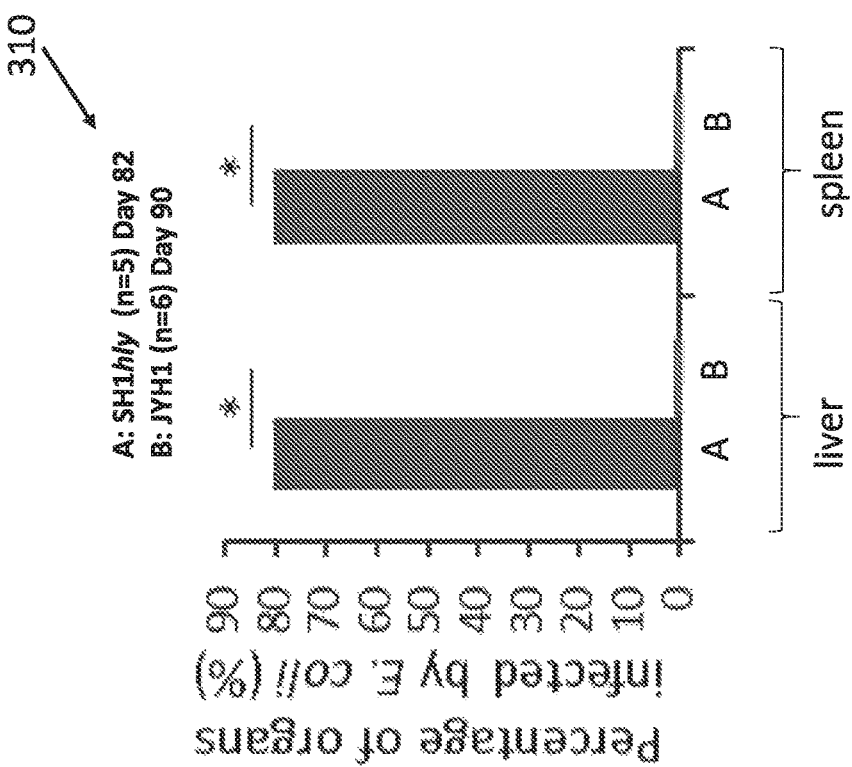
FIG. 3B shows percentages of liver and spleen infected by the bacterial strains JYH1 and SH1 hly in nude mice carrying subcutaneous SW480 tumors in accordance with an example embodiment.
Figure 3A:
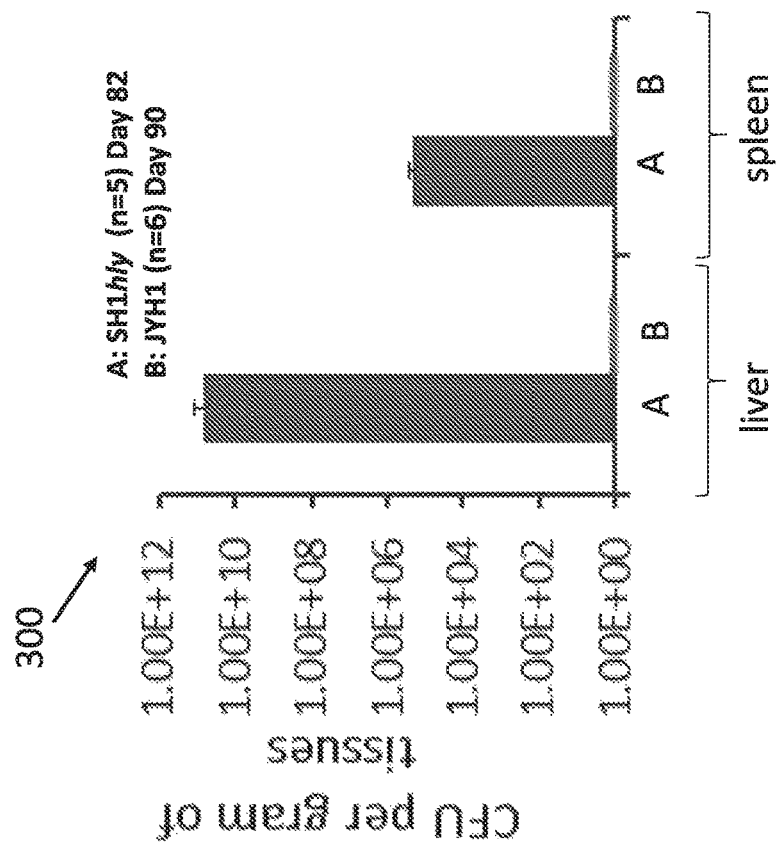
FIG. 3A shows colonization of the bacterial strains JYH1 and SH1 hly in liver and spleen of nude mice carrying subcutaneous SW480 (a human colorectal cancer cell line) tumors in accordance with an example embodiment.

FIGS. 3A and 3B show *E. coli* JYH1 specifically targeted SW480 tumors and did not colonize normal tissues in nude mice, while its isogenic strain SH1 hly that was not engineered by the tumor-targeting nucleotide system colonized both tumors and normal tissues. *P<0.05. Error bar, SEM.

FIG. 3A shows CFU 300 per gram of liver and spleen tissues in nude mice with SW480. FIG. 3B shows percentage 310 of liver and spleen organs infected by JYH1 and SH1 hly. As shown in FIGS. 3A and 3B, JYH1 did not colonized liver or spleen. The livers, spleens, hearts, lungs, kidneys of all the JYH1-treated nude mice were all cleared of JYH1, indicating that the glucose-sensing module is able to confine JYH1 to tumors and prevent it from spreading to distant organs for a long time. In contrast to JYH1, its isogenic strain SH1 hly that is not equipped with the glucose-sensing module colonized not only tumors ($9.35 \times 10^8 \pm 5.97 \times 10^8$ cfu/g, mean±SEM) but also organs. The livers ($6.0 \times 10^{10} \pm 6.0 \times 10^{10}$ cfu/g, mean±SEM) and spleens ($1.85 \times 10^5 \pm 9.74 \times 10^4$ cfu/g, mean±SEM) of four SH1 hly-treated mice (80%, 4 out of 5) were infected by SH1 hly when analyzed on day 82.

Figure 3C:
FIG. 3C shows liver abscess developed in a mouse treated with the bacterial strain SH1 hly in accordance with an example embodiment.

Among the infected mice, one mouse developed liver abscess as shown in FIG. 3C. The picture 320 was taken on day 82 when the mouse was euthanized for analysis.

Figure 3D:
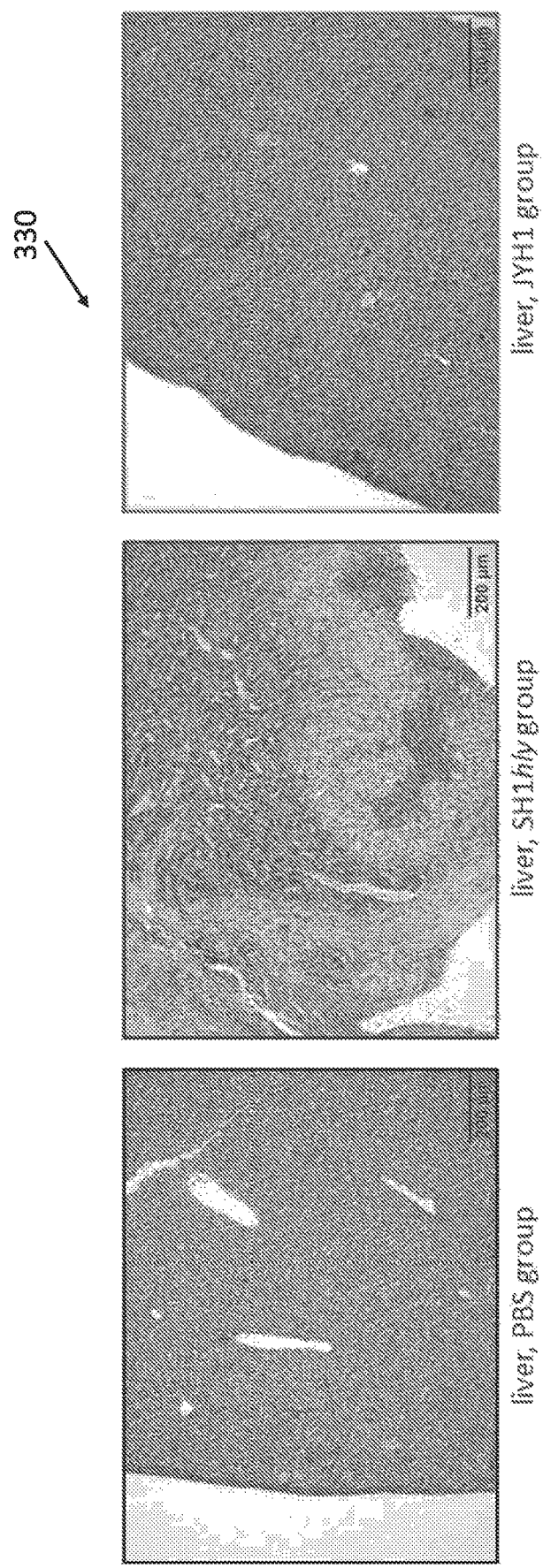
FIG. 3D shows microscopic images of Hematoxylin and Eosin (H&E)-stained liver sections from nude mice carrying subcutaneous SW480 tumors that are treated with Phosphate-buffered saline (PBS), strains SH1hly and JYH1 in an accordance with an example embodiment.

Tumor specificity of JYH1 and its requirement of the glucose-sensing, tumor-targeting nucleic acid system were also confirmed by Hematoxylin and Eosin (H&E) staining of liver sections 330, which showed that the liver of JYH1-treated mice was normal whereas massive inflammatory infiltration and abscess occurred in the liver of SH1 hly-treated mice as shown in FIG. 3D (Scale bar, 200 μm). Taken together, these data demonstrate that the glucose-sensing tumor-targeting nucleic acid system optimizes tumor specificity of JYH1 in nude mice.

EXAMPLE 5

Figure 4:
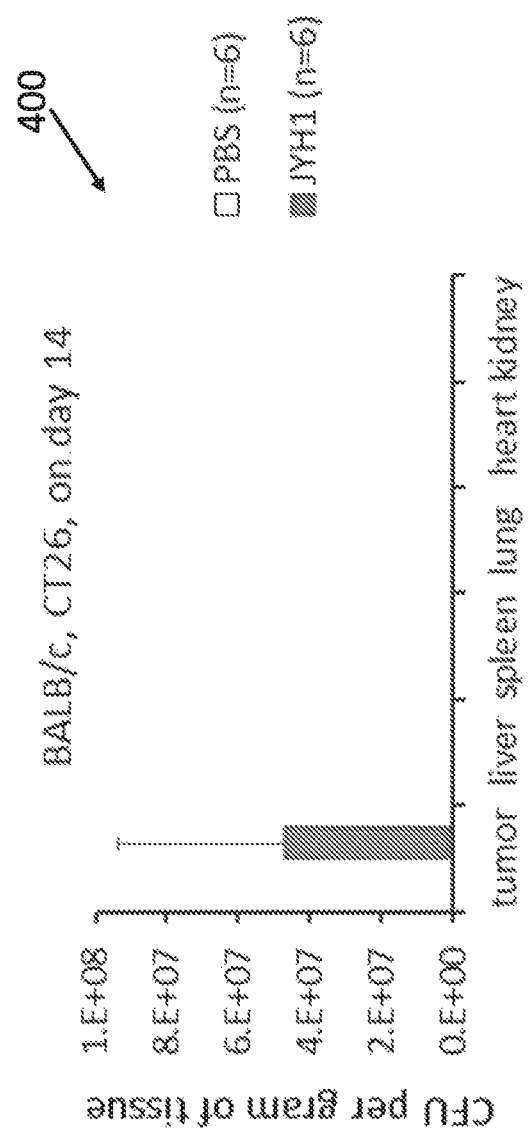
FIG. 4 shows the targeting efficacy of intravenously injected strains JYH1 on CT26 tumors of immunocompetent BALB/c mice in accordance with an example embodiment.

The ability of JYH1 in specifically colonizing tumors in immunocompetent mice was tested. JYH1 was intravenously administered to immunocompetent BALB/c mice carrying CT26 tumors. 14 days after the bacterial injection, all the mice were euthanized due to excessive tumor growth. FIG. 4 shows CFU 400 per gram of normal tissues and CT26 tumors in BALB/c mice. Plating analysis of homogenized tissues showed that the intravenously injected JYH1 did not colonize any organs tested including the liver, spleen, heart, lung and kidney of the immunocompetent mice on day 14. In contrast, levels of JYH1 in the tumors reached $4.67 \times 10^7$ cfu per gram ($\pm 1.62 \times 10^7$ cfu/g) as shown in FIG. 4. These together with the data from the nude mice demonstrate that JYH1 specifically targets solid tumors regardless of the integrity of the immune system.

Figure 5:
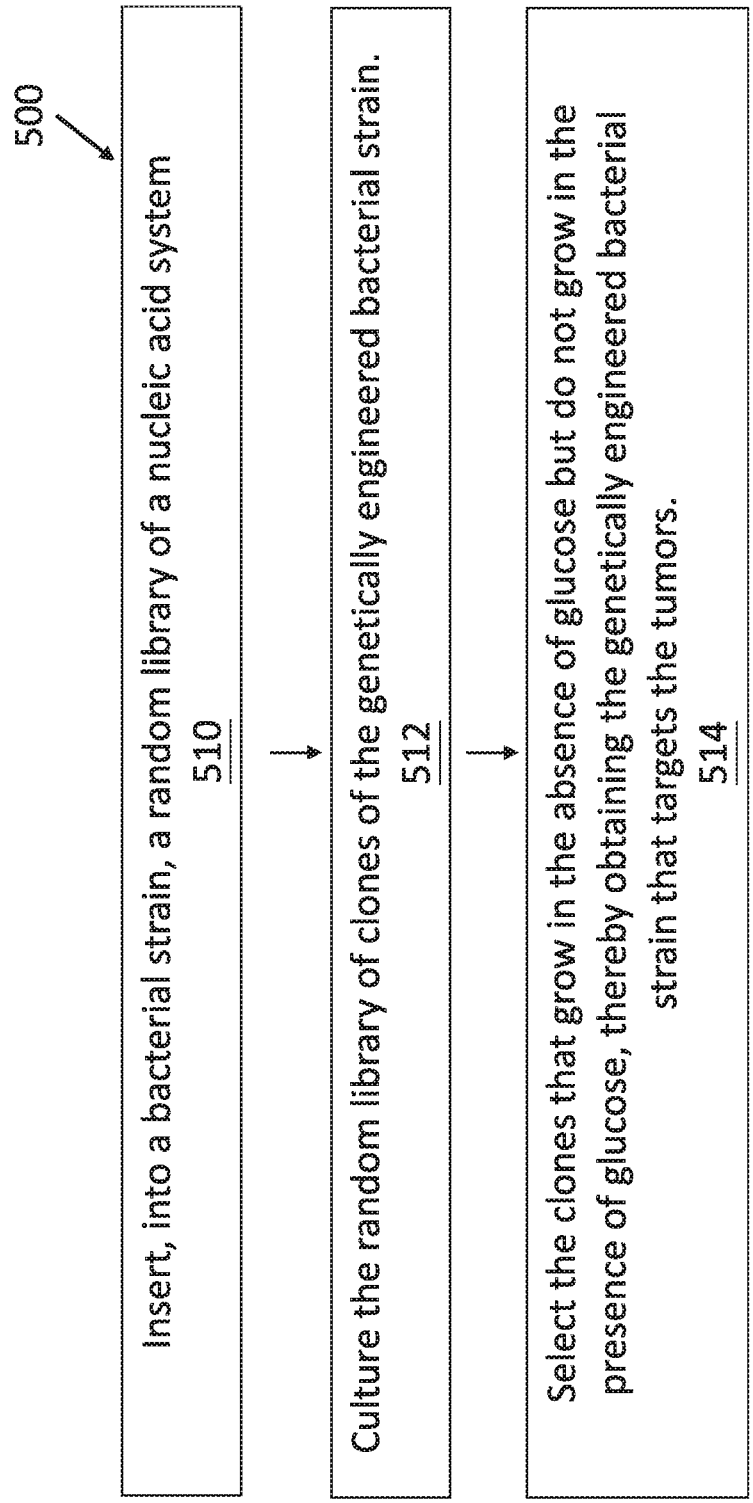
FIG. 5 show a method to construct a genetically engineered bacterial strain that targets solid tumors by selectively living and growing in glucose-deprived regions in accordance with an example embodiment.

FIG. 5 shows a method 500 of constructing a genetically engineered bacterial strain that targets solid tumors by selectively growing in glucose-deprived environments.

Block 510 states inserting into a bacterial strain a random library of a nucleic acid system.

In an example embodiment, the nucleic acid system includes a first DNA fragment that encodes a toxin, a second DNA fragment that encodes an antidote that negates the toxin. The nuclei acid system also includes a first promoter that controls transcription of the second DNA fragment. The nucleic acid system also includes a first constitutive promoter that causes constitutive expression of the first DNA fragment.

In an example embodiment, the nucleic acid system includes a first DNA fragment that encodes a toxin, a second DNA fragment that encodes an antidote that negates the toxin. The nuclei acid system also includes a second promoter that controls transcription of the first DNA fragment. The nucleic acid system also includes a second constitutive promoter that causes constitutive expression of the second DNA fragment.

In an example embodiment, the toxin-antidote pair includes but is not limited to the CcdB-CcdA pair. Other toxin-antidote pairs such as AvrRxo1-Arc1, Hha-TomB, and PaaA2-ParE2 can be used to replace the CcdB-CcdA pair. In an example embodiment, the first promoter includes but is not limited to the lac promoter. The lac promoter can be replaced by other glucose-repressed promoters such as the promoters of gltA, sdhADC or tnaB. In an example embodiment, the second promoter includes but is not limited to the promoter of ptsG, the promoter of fruB and the promoter of ackA.

In an example embodiment, a random sequence that consists of 5-6 nucleotides is inserted to replace the native 5-6 nucleotides immediately upstream of the start codon of the ccdA gene and downstream of the first promoter.

In an example embodiment, a random sequence that consists of 5-6 nucleotides is inserted to replace the native 5-6 nucleotides immediately upstream of the start codon of the ccdB gene and downstream of the second promoter.

Block 512 states culturing the random library of the clones of the genetically engineered bacterial strain.

In an example embodiment, the nucleic acid system is grafted into the chromosome of the bacterial strain. In an example embodiment, the nucleic acid system is grafted into a plasmid and the plasmid is inserted into the bacterial strain. In an example embodiment, the bacterial strain includes but is not limited to *Escherichia coli* MG1655. Other *Escherichia coli* strains such as DH5α and CFT073 and other Gram-negative bacterial species such as *Salmonella* and *Shigella* may be used to replace MG1655. In an example embodiment, clones of the bacterial strain that includes the nucleic acid system are cultured on LB agar with or without glucose.

Block 514 states selecting the clones that grow in the absence of glucose but do not grow in the presence of glucose, thereby obtaining the genetically engineered bacteria strain that targets the tumors.

In an example embodiment, the clones that grow in LB agar without glucose but do not grow in LB agar with 5 mM glucose are selected and identified as potential candidates of tumor-targeting bacteria.

In an example embodiment, the clones that grow in M63 agar without glucose but do not grow at glucose concentrations of 1-4 mM are confirmed as potential candidates of tumor-targeting bacteria.

In an example embodiment, the method further includes generating a random library of the nucleic acid system by inserting a random sequence that consists of 5-6 nucleotides to replace native nucleotides that are located immediately upstream of the second DNA fragment, when the nucleic acid system includes the first promoter.

In an example embodiment, the method further includes generating a random library of the nucleic acid system by inserting a random sequence that consists of 5-6 nucleotides to replace native nucleotides that are located immediately upstream of the first DNA fragment, when the nucleic acid system includes the second promoter.

EXAMPLE 6

In this example, the inhibitory effects of intravenously injected E. coli JYH1 on tumor growth in vivo were evaluated.

FIG. 6A shows the inhibitory effect 700 of intravenously injected E. coli JYH1 on the growth of HCT116 tumors in nude mice. Intravenous injection of JYH1 repressed growth of HCT116 tumors in nude mice. In contrast, JY1 had little effects on the tumor growth compared to the PBS control. The HCT116 tumors of JY1-treated mice grew equally well with those of PBS-treated controls, whereas the HCT116 tumors of JYH1-treated mice grew relatively slowly and 50% of them (5 out of 10) started to regress 18-26 days after the intravenous injection of the bacteria ($10^7$/mouse). JYH1 displayed inhibitory effects on HCT116 tumor growth of 100% of the tested mice (n=10), demonstrating a significantly better antitumor efficacy than JY1 (Fisher's Exact test, $p<0.0001$).

Figure 6D:
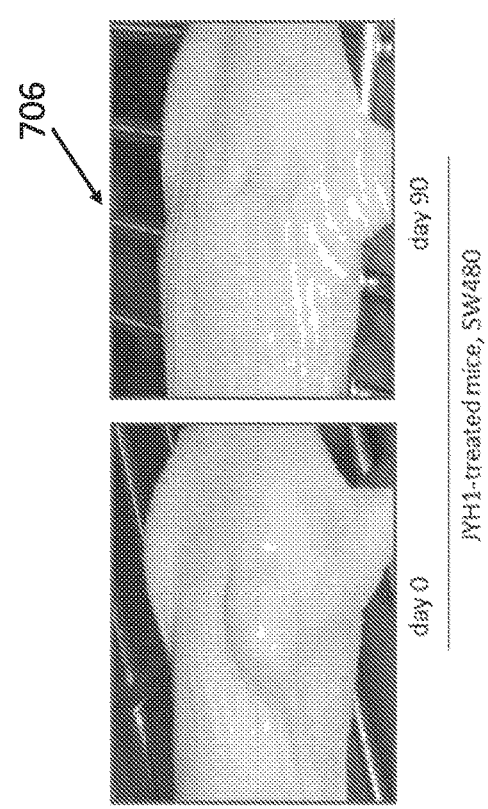
FIG. 6D shows a representative photo of SW480 tumors treated by intravenous injection of JYH 1 in mice from 0-90 days in accordance with an example embodiment.
Figure 6C:
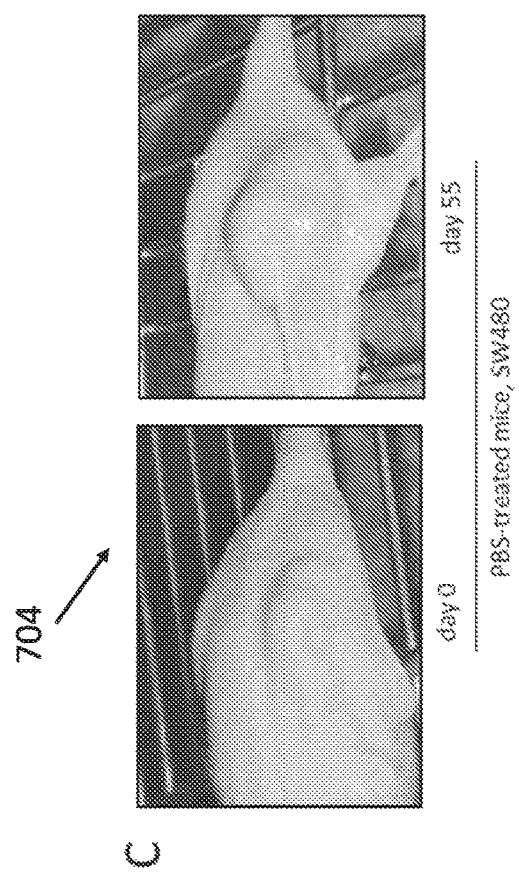
FIG. 6C shows a representative photo of SW480 tumors treated by intravenous injection of PBS in mice from 0-55 days in accordance with an example embodiment.

FIG. 6B shows an analysis 702 for the inhibitory effect of intravenously injected E. coli JYH1 on the growth of SW480 tumors in nude mice. FIG. 6C shows representative photos 704 of a SW480 tumor in PBS-treated mice from 0 and 55 days. FIG. 6D shows representative photos 706 of a SW480 tumor in JYH 1-treated mice from 0 and 90 days. Growth of the SW480 tumors was monitored for as long as 90 days. Tumors of the JYH1-treated mice (n=6) regressed 26-52 days after the intravenous injection of JYH1, with the effective percentage being 100%. Among these, tumors of 66.7% of the mice (4 out of 6) disappeared and did not relapse by the end of the experiments. The tumor of one of the remaining two mice was not cured but kept quiescent. The tumor of only one mouse relapsed (16.67%, 1 out of 6). In contrast, none of the PBS-treated tumors regressed or disappeared. These data further showed that JYH1 has significant repressive effects on tumor growth in vivo.

Therefore, in an example embodiment, bacteria that are toxic to both tumor cells and normal tissue cells can become specific to tumors and repress tumor growth without affecting normal tissues, when the bacteria are equipped with the tumor-targeting nucleic acid system.

EXAMPLE 7

In this example, the cytotoxin-encoding genes (i.e. the genes encoding cytotoxin) are cloned in a pBAD plasmid. Genes encoding each of the cytotoxin were individually cloned into a pBAD plasmid. In the case of exlA of P. aeruginosa, nhe of B. cereus and hlyA of V. cholera (hereafter referred to as VhlyA), the pelB leader sequence was fused in frame to the upstream of the target genes to allow for the excretion of the encoded cytotoxins. A constitutive promoter was used to drive the transcription of the fused DNAs. In the case of the hlyCABD operon (hereafter referred to as hlyCABD) coding for E. coli alpha-hemolysin, the entire operon was cloned into the pBAD vector. The pelB leader sequence was not employed for the hlyCABD operon in that the products of the operon include not only the hlyA hemolysin but also the secretion system required for the hemolysin secretion. Sequencing analyses of resulting recombinant plasmids verified that all the four genes were correctly cloned.

In one example embodiment, the pelB leader sequence is shown in SEQ ID No. 9. The sequence of exlA with the pelB leader is shown in SEQ ID No. 10. The sequence of Nhe with the pelB leader is shown in SEQ ID No. 11. The sequence of hlyA of Vibrio cholera with pelB leader is shown in SEQ ID No. 12. The sequence of hlyBACD operon of E. coli is shown in SEQ ID No. 13.

EXAMPLE 8

In this example, the cloned genes of Example 7 were shown to produce functional cytotoxins and kill cancer cells in vitro assays.

Figure 7:
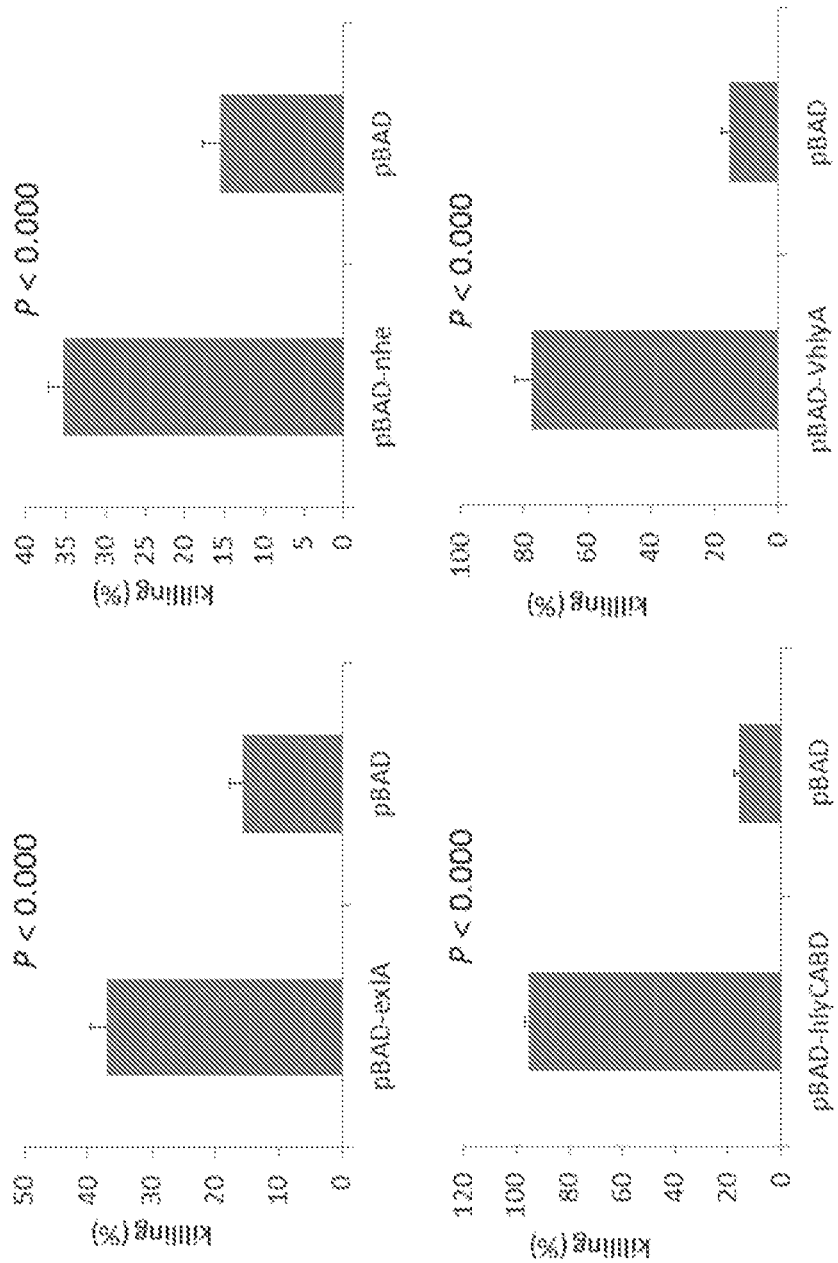
FIG. 7 shows an in vitro cytotoxicity assay in accordance with an example embodiment illustrating that the plasmid-derived production of cytotoxins ExIA, Nhe, E. coli alpha-hemolysin and V. cholera hemolysin A are cytotoxic to the cancer cell line B16F10. pBAD, an empty plasmid serving as a negative control; hlyCABD, the operon encoding for E. coli alpha-hemolysin and its secretion system; Vhly, the gene encoding V. cholera hemolysin A. Error bar, SD.

Each of the recombinant plasmid was introduced into an E. coli reference strain TOP10. This strain per se does not cause cell lysis and, therefore, any killing action has to be attributed to the toxin production from the plasmid that the strain carries. The murine melanoma cell line B16F10 was used for the in vitro cytotoxicity assay. The B16F10 cells were co-cultured with E. coli TOP10 carrying each of the four recombinant plasmids at a moi of 100 (i.e. 100 bacteria per cell). As controls, the cells were also co-cultured with TOP10 carrying an empty pBAD plasmid or PBS. After 12 hours of co-incubation, TOP10 carrying recombinant plasmids with the toxin-encoding genes displayed significant cytotoxic effects on B16F10 cells whereas TOP10 with the empty plasmid had little effects on the cell viability as shown in FIG. 7.

Figure 8:
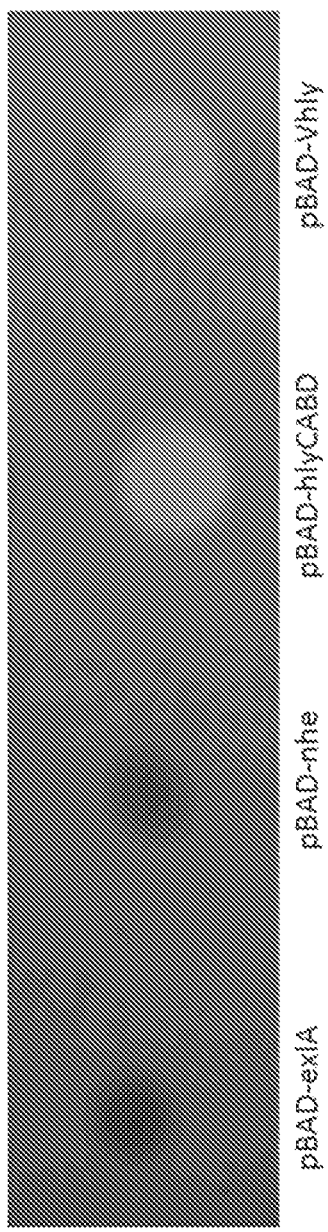
FIG. 8 shows hemolytic activity of the plasmid-derived E. coli alpha-hemolysin and V. cholera hemolysin A in accordance with an example embodiment. HlyCABD, the operon coding for E. coli alpha-hemolysin and its secretion system; Vhly, the gene encoding V. cholera hemolysin A. All the plasmids were introduced into a non-pathogenic and non-hemolytic E. coli reference strain TOP10.

These in vitro data verified that the genes cloned into the pBAD plasmid successfully produced cytotoxins to kill cancer cells. Among the four cytotoxins, the two hemolysins are hemolytic whereas the other two toxins are not. In agreement with this, TOP10 with pBAD-hlyCABD and TOP10 with pBAD-VhlyA caused hemolysis on blood agar while TOP10 carrying pBAD-exlA or pBAD-nhe did not (as shown in FIG. 8). The hemolysis assays confirmed the functionality of the genes cloned in the plasmids.

EXAMPLE 9

In this example, the cytotoxins are shown to enhance anticancer efficacy of bacteria in vivo.

The anticancer ability of bacteria that were transformed to overexpress each of the above-mentioned cytotoxins was assessed. JYH1 is an E. coli strain with intrinsic ability to moderately repress tumor growth. Each of the four recombinant plasmids was separately introduced into JYH1 to analyze if any of them enhanced the anticancer efficacy of JYH1.

Figure 9:
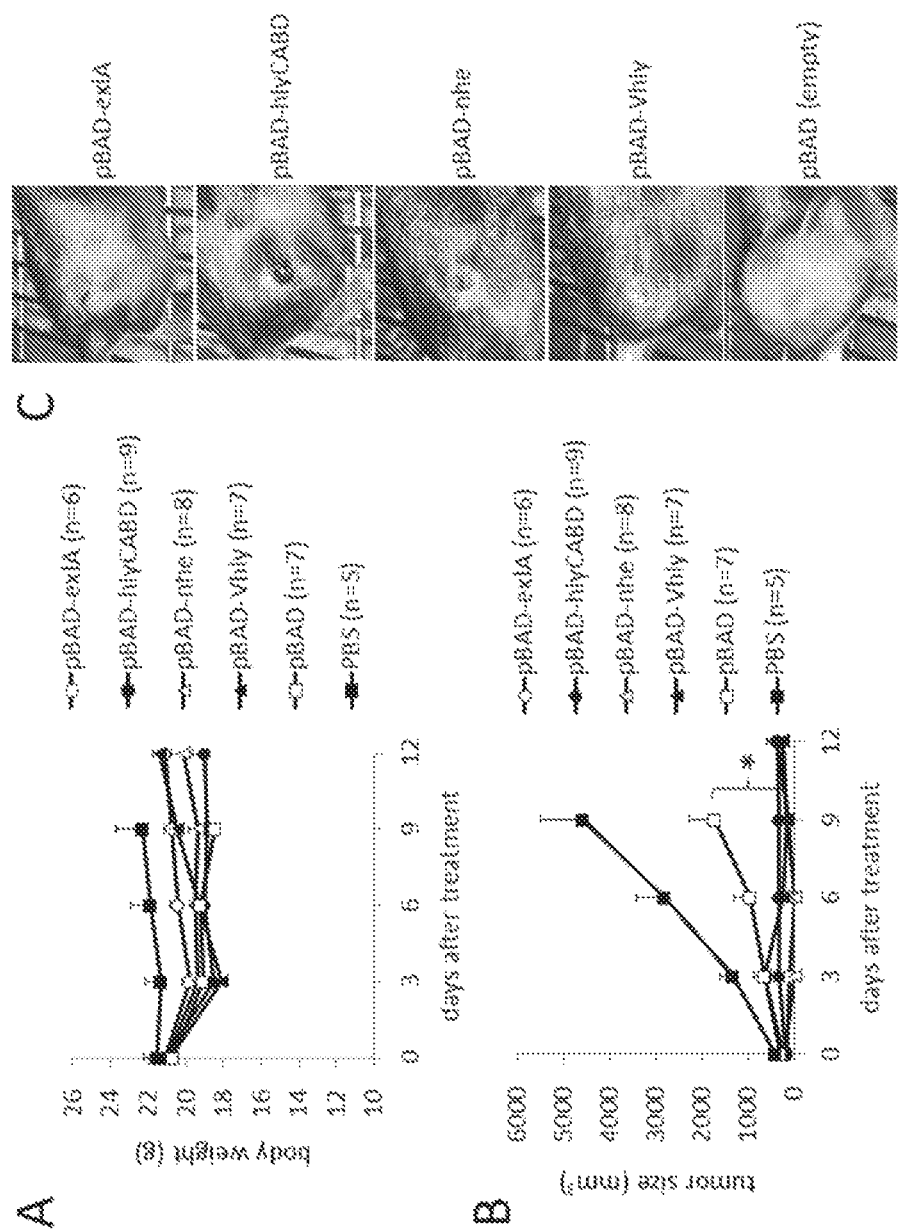
FIG. 9 shows that cytotoxins enhance the inhibitory ability of E. coli on murine syngeneic tumors in immunocompetent mice. A single dose of E. coli with or without expressing various cytotoxins was injected into murine melanoma B16F10 tumors in C57BL/6N mice. (A) Body weight of the mice over time. Error bar, SEM. (B) Effects of intratumorally injected bacteria (5 $10^7$/mouse) on tumor growth. The mice treated with bacteria carrying the empty plasmid pBAD and those treated with PBS (negative controls) were euthanized on day 9 after tumor measurement due to excessive tumor growth. Error bar, SEM. *, P<0.05. (C) Representative photos of the B16F10 tumors injected with E. coli expressing the cytotoxins tested or E. coli carrying an empty vector pBAD on day 9 (i.e. 9 days after tumor challenge).

In C57BL/6N mice, subcutaneous B16F10 tumors that were intratumorally injected with JYH1 overexpressing any of the four cytotoxins grew much more slowly than JYH1 carrying the empty plasmid (all $P<0.05$). The cytotoxin-treated tumors regressed during the first 6 or 9 days after the treatment, while those treated with phosphate buffer saline (PBS) or JYH1 carrying the empty plasmid grew readily without regression (as shown in FIG. 9).

Figure 10:
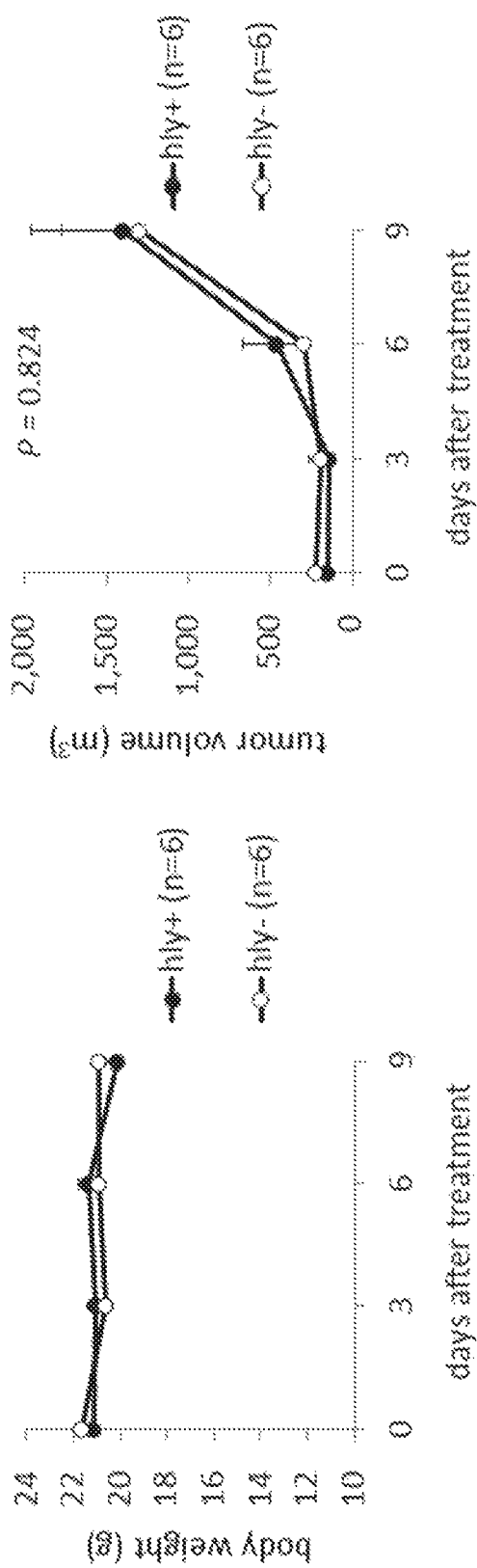
FIG. 10 shows that production of E. coli alpha-hemolysin from the single copy of the hlyCABD operon in the chromosome is not required for the anticancer efficacy of hemolytic E. coli. A single dose of the bacteria ($1\times10^7$ cfu per tumor) was injected into murine melanoma B16F10 tumors of C57BL/6N mice. hly+, an hemolytic E. coli strain carrying the hlyCABD operon in the chromosome; hly-, its isogenic mutant deleted for the entire hlyCABD operon. Error bar, SEM.

Among the four cytotoxins, alpha-hemolysin is naturally produced by some E. coli strains. Deletion of the chromosomal gene encoding alpha hemolysin did not impair the ability of E. coli to repress tumor growth (as shown in FIG. 10). This indicates that the intrinsic anticancer action of the hemolytic E. coli strains such as JYH1 is not dependent on their natural production of alpha-hemolysin from the chromosome. However, plasmid-derived overproduction of alpha-hemolysin enhanced the anticancer efficacy of these bacteria, as shown in FIG. 9. alpha-hemolysin produced from a single copy of the operon in the chromosome is insufficient for tumor inhibition but its overproduction from a multi-copy plasmid is sufficient for the cytotoxin to significantly repress tumor growth.

Cytotoxins Pseudomonas aeruginosa exolysin, Bacillus cereus non-hemolytic enterotoxin and Vibrio cholera hemolysin A are not naturally produced by E. coli, but engineering E. coli to produce these cytotoxins enhances anticancer efficacy of *E. coli*.

In an example embodiment, *E. coli* was made to produce the non-*E. coli* derived cytotoxins by introducing plasmids carrying the genes encoding the cytotoxins into *E. coli*. In an example embodiment, the cytotoxin-encoding genes are inserted into the chromosome of *E. coli* to increase the anticancer efficacy. In an example embodiment, the cytotoxins improve the anticancer efficacy of bacteria other than *E. coli*.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, "immediately", "immediately upstream" or "immediately downstream", means that there are no other nucleotides between one DNA fragment and another DNA fragment.

As used herein, "system" refers to a combination or a genetic circuit that includes the toxin gene, the antidote gene and their respective promoters. The toxin gene and the antidote gene of the system may be placed in any order. The toxin gene and the antidote gene of the system may be located in the same molecule or in different molecules. In an example embodiment, one of the toxin gene and the antidote gene may be in the chromosome of a bacterium while the other gene may be in a plasmid in the same bacterium.

As used herein, "at the tumor tissue" can be interchanged with terms such as "in the tumor", "at the tumor site", "inside the tumor", "at areas of the tumor tissue". These terms refer to being located in an area where tumor cells are present and where the local environment is low in glucose.

What is claimed is:

1. A bacterium for targeting tumors and treating cancer, each comprising:
   a nucleic acid system; and
   a gene that encodes a cytotoxin that kills tumor cells, wherein the nucleic acid system comprises:
   a first DNA fragment that encodes a toxin that kills the bacterium;
   a second DNA fragment that encodes an antidote that negates the toxin, the second DNA fragment being transcribed at tumor tissues but not transcribed at non-tumor tissues;
   a promoter of an antidote gene that is operably linked to the second DNA fragment and represses transcription of the second DNA fragment under control of a glucose level such that the antidote is expressed at the tumor tissues but not expressed at the non-tumor tissues; and
   a constitutive promoter of a toxin gene that is operably linked to the first DNA fragment and causes constitutive transcription of the first DNA fragment such that the toxin is expressed at the tumor tissues and the non-tumor tissues;
   wherein a random sequence that consists of 5-6 nucleotides that replaces the original 5-6 nucleotides of the genetically engineered bacterial strain is located immediately upstream of the second DNA fragment;
wherein a pair of the toxin and the antidote is selected from the group consisting of a CcdB-CcdA pair, an AvrRxo1-Arc1 pair, a Hha-TomB pair, and a PaaA2-ParE2 pair;
wherein the second DNA fragment is transcribed at a glucose environment with a concentration lower than 0.424 mM but not transcribed at a glucose environment with a concentration higher than 1.22 mM; and
wherein the random sequence is GCCTT or TGTCT.

2. The bacterium according to claim 1, wherein the cytotoxin that kills tumor cells is selected from a group consisting of *Pseudomonas aeruginosa* exolysin, *Bacillus cereus* non-hemolytic enterotoxin, *Vibrio cholera* hemolysin A and *Escherichia coli* alpha-hemolysin.

3. The bacterium according to claim 1, wherein the promoter of the antidote gene is located immediately upstream of the second DNA fragment.

4. The bacterium according to claim 1, wherein the constitutive promoter of the toxin gene is located immediately upstream of the first DNA fragment.

5. The bacterium according to claim 1, wherein the promoter of the antidote gene is selected from a group consisting of a lac promoter, a gltA promoter, an sdhADC promoter and a tnaB promoter.

6. The bacterium according to claim 1, wherein the first DNA fragment is shown as SEQ ID No:1, and the second DNA fragment is shown as SEQ ID No:2.

7. The bacterium according to claim 1, wherein the promoter of the antidote gene is shown as SEQ ID No:3.

8. The bacterium according to claim 1, wherein the bacterium further includes a third DNA fragment that encodes a chloramphenicol resistance cassette, wherein the third DNA fragment is shown as SEQ ID No:4.

9. The bacterium according to claim 1, wherein the bacterium is derived from a bacterial strain selected from a group consisting of *Escherichia coli, Salmonella* and *Shigella*.

10. The bacterium according to claim 1, wherein the bacterium is derived from *Escherichia coli* MG1655.

11. The bacterium according to claim 1, wherein the nucleic acid system is shown as SEQ ID No:7 or SEQ ID No:8.

12. The bacterium according to claim 1, wherein the bacterium is derived from a strain JY1 deposited at the China General Microbiological Culture Collection Center (CGMCC) under deposit no. 14577, a strain JY6 deposited at CGMCC under deposit no. 14578, a strain SH1 deposited at CGMCC under deposit no. 14580, or a strain deposited at CGMCC under deposit no. 14579.

13. A drug delivery composition, comprising the bacterium of claim 1.

14. A method of treating a cancer patient with solid tumor, comprising administering an effective amount of the bacterium of claim 1 or the drug delivery composition of claim 13 to a patient in need thereof.

15. The method according to claim 14, wherein the solid tumor is melanoma or colorectal cancer.

* * * * *